(12) United States Patent
Ahn et al.

(10) Patent No.: US 11,214,715 B2
(45) Date of Patent: Jan. 4, 2022

(54) IONIC POLYMERS AND THEIR USE AS WET-ADHESIVES AND COATINGS

(71) Applicant: ACatechol, Inc., Santa Barbara, CA (US)

(72) Inventors: Byung Jun Ahn, Goleta, CA (US); Sam Linh Nguyen, Saratoga, CA (US); Roscoe Linstadt, Palo Alto, CA (US)

(73) Assignee: ACatechol, Inc., Santa Barbara, CA (US)

( * ) Notice: Subject to any disclaimer, the term of this patent is extended or adjusted under 35 U.S.C. 154(b) by 0 days.

(21) Appl. No.: 16/521,154

(22) Filed: Jul. 24, 2019

(65) Prior Publication Data

US 2020/0056076 A1 Feb. 20, 2020

Related U.S. Application Data

(62) Division of application No. 15/621,453, filed on Jun. 13, 2017, now Pat. No. 10,435,599.

(Continued)

(51) Int. Cl.
| | |
|---|---|
| *A61C 5/00* | (2017.01) |
| *C08G 61/04* | (2006.01) |
| *C09J 139/04* | (2006.01) |
| *C09J 139/08* | (2006.01) |
| *A61L 24/06* | (2006.01) |
| *C09J 123/00* | (2006.01) |

(52) U.S. Cl.
CPC ............ *C09J 139/04* (2013.01); *A61L 24/06* (2013.01); *C09J 123/00* (2013.01); *C09J 139/08* (2013.01)

(58) Field of Classification Search
CPC ..................................... A61C 5/00; A61C 5/04
USPC ............................. 433/228.1, 226, 215; 520/1
See application file for complete search history.

(56) References Cited

U.S. PATENT DOCUMENTS

2011/0135850 A1* 6/2011 Saha .................. G02B 1/04
428/1.23

* cited by examiner

*Primary Examiner* — Jessica Whiteley
(74) *Attorney, Agent, or Firm* — HDC IP Law, LLP; Sam L. Nguyen

(57) ABSTRACT

The present application discloses an adhesive composition comprising a polymer of the formulae A, B and C:

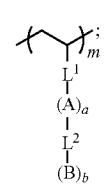

A

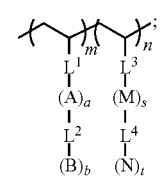

B

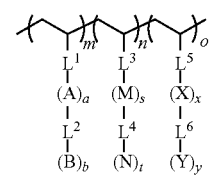

C and methods for using the adhesive composition.

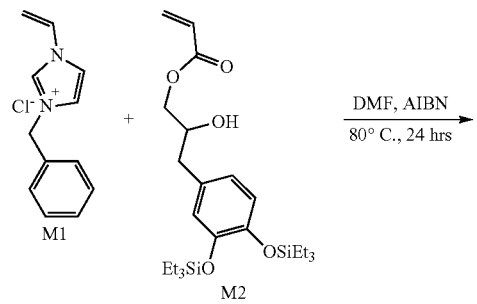

a)

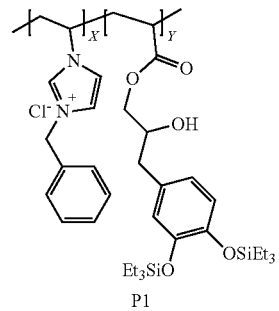

P1

(Continued)

-continued
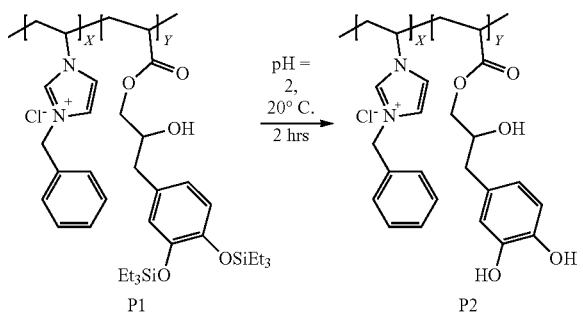
b)
wherein x and y define the block polymer and are integer greater than 1.
3 Claims, No Drawings
Related U.S. Application Data
(60) Provisional application No. 62/363,605, filed on Jul. 18, 2016, provisional application No. 62/349,328, filed on Jun. 13, 2016.

IONIC POLYMERS AND THEIR USE AS WET-ADHESIVES AND COATINGS

RELATED APPLICATIONS

The present application is a Divisional Application of U.S. Non-Provisional application Ser. No. 15/621,453 filed on Jun. 13, 2017, issued as U.S. Pat. No. 10,435,599 on Oct. 8, 2019, which claims priority to U.S. Provisional Application No. 62/349,328 filed Jun. 13, 2016, and U.S. Provisional Application No. 62/363,605 filed Jul. 18, 2016, the contents of which are incorporated herein by reference.

BACKGROUND

Phase transitions of aqueous solutions of charged polymers and proteins have been reported. See Wei, W.; Waite, J. H. et al., A mussel-derived one component adhesive coacervate. *Acta Biomater* 2014, 10 (4), 1663-1670; Ahn, B. K.; Das; Lipshutz, B. H.; Israelachvili, J. N.; Waite, J. H. et al., High-performance mussel-inspired adhesives of reduced complexity. *Nat Commun*, 2015, 6; J. N.; Waite, J. H.; Ahn, B. K. et al., Microphase Behavior and Enhanced Wet-Cohesion of Synthetic Copolyampholytes Inspired by a Mussel Foot Protein. *J Am Chem Soc*, 2015, 137 (29), 9214-9217; Brangwynne, C. P. et al., Polymer physics of intracellular phase transitions. *Nat Phys*, 2015, 11 (11), 899-904. Cation-π interaction is strong in aqueous media and may be used for wet-adhesion in biology. See Lu, Q., et al., Adhesion of mussel foot proteins to different substrate surfaces. Journal of the Royal Society Interface, 2013, 10 (79).

SUMMARY OF THE INVENTION

In one aspect of the present application, there is disclosed compositions and methods for generating glue, coating or adhesive, such as wet-glue or wet-tack coating, to bind to or coat materials. As used herein, wet-tack refers to the tackiness of a composition, a material or an adhesive in a wet environment. In another aspect, the adhesion may be based, in part, on ionic interactions, such as cation-t interaction.

In one embodiment, the present application discloses an adhesive composition comprising a polymer of the formulae A, B and C:

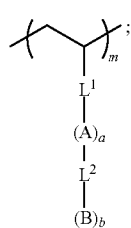

A

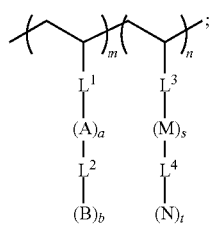

B

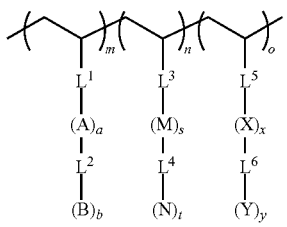

C wherein: each m, n and o is independently 100 to 1,000,000;
each a, b, s, t, x and y is independently 0, 1 or 2;
each $L^1$, $L^2$, $L^3$, $L^4$, $L^5$ and $L^6$ is independently absent or is selected from the group consisting of —$CH_2$—, —O—, —S—, —$(CH_2)_{1-2}$—, —$CH(CH_2$—$)_2$—, —C(O)O—, —C(O)O$CH_2$—, —$CH_2$C(O)O—, —$CH_2$C(O)NH—, —C(O)NH$CH_2$—, —C(O)NH— and —NR'— where R' is selected from H, —$CH_3$, —$CH_2CH_3$ and —$CH_2C_6H_5$ or substituted benzyl, or a bond;
each A, B, M, N, X and Y is independently absent or selected from the group consisting of an aryl, substituted aryl, aryl ammonium, heteroaryl, substituted heteroaryl, heteroarylammonium $X^-$ and substituted heteroarylammonium $X^-$, wherein each $X^-$ is independently a counter anion selected from $Cl^-$, $Br^-$, $I^-$, —$SO_4^{-2}$ and —$PO_4^{-3}$;
provided that not all of $L^1$, $L^2$, $L^3$, $L^4$, $L^5$ and $L^6$, and A, B, M, N, X and Y are absent;
provided that for Formula A, only one of A, B is a heteroarylammonium $X^-$ or a substituted heteroarylammonium $X^-$; and provided that when $L^1$ is —$(CH_2)_{1-2}$— or a bond, then the group -$(A)_a$-$L^2$-$(B)_b$ is not a group selected from -heteroarylammonium $(X^-)$-$L^2$-dihydroxy-phenyl, a substituted or unsubstituted imidazole and a substituted or unsubstituted imidazolinium $(X^-)$; or arylammonium $(X^-)$-$L^2$-dihydroxy-phenyl, a substituted or unsubstituted amine or a substituted ammonium $(X^-)$ group. In one variation, at least one, two or three of $L^1$, $L^2$, $L^3$, $L^4$, $L^5$ and $L^6$, and A, B, M, N, X and Y are present. As used herein, an asymmetric linker (e.g., $L^1$, $L^2$ etc) or group designated as "—C(O)O—" for example, represents both the divalent groups "—C(O)O—" and "—OC(O)—" that may be inverted and may attach or link in both directions.

In one variation of the adhesive, the molar ratio of the monomer in the polymer or copolymer is 1:0, 1:1, or 1:1:1. In another variation of the compound or adhesive, the ratio of m:n is 1:0 or 1:1; and the ratio of m:n:y is 1:1:1. In another variation, m+n=100 mol %; m: 100-0 mol %; n: 0-100 mol %. In another variation, m+n+y=100 mol %; m: 100-0, n: 0-100 and z: 0-100.

In one variation of the above adhesive, the adhesive is formulated in water. In another variation of the above, -$(A)_a$- is not a group selected from an ammonium, imidazolium or pyridinium group. In another variation, -$(A)_a$- is a group selected from quinolinium, isoquinolinium, phenanthridinium, phenanthrolinium, pyrimidinium, benzothiazolinium, benzimidazolium, benzothiadiazolinium, purinium, pyrazinium or acridinium. In another variation of the above, the polymer is prepared from a monomer; and is not a co-polymer. In one variation, at least one of the -A- and —B— groups is a curable group. In another variation, at least one of A, B, N and Y is a curable group.

In one aspect, there is provided an adhesive composition comprising a curable side chain of the formulae A', B' and C':

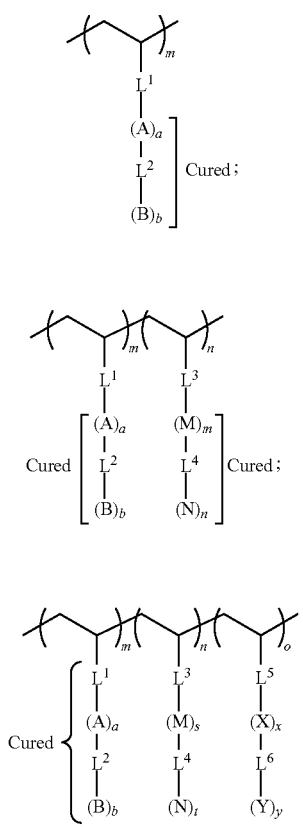

wherein the polymer is further curable.

It is noted that the above depiction of the copolymers, designated as the -L$^1$-(A)$_a$-L$^2$-(B)$_b$ monomer and the -L$^3$-(M)$_m$-L$^4$-(N)$_n$ monomer, the designation is used only to distinguish the structures and functional groups of the linkers and functional groups, and is not intended to show any particular sequence of the copolymers. The copolymers may be random, alternating, statistical, periodic and block copolymers. In one variation, at least one of the -A-, —B—, -M, —N, —X and —Y group is a curable group.

In one variation of the above, at least one of -(A)$_a$-, -(M)$_m$- and —(X)$_x$— is not a group selected from an ammonium, imidazolium and pyridinium. In another variation, at least one of -(A)$_a$-, -(M)$_m$- and —(X)$_x$— is independently selected from the group consisting of quinolinium, isoquinolinium, phenathridinium, phenanthrolinium, pyrimidinium, benzothiazolinium, benzimidazolium, benzothiadiazolinium, purinium, pyrazinium or acridinium. In another variation, the polymer is prepared from a monomer; and is not a copolymer. In one variation, at least one of the -A- and —B— group is a curable group. In another variation, at least one of B, N or Y is a curable group.

In one variation of the polymers of the present disclosure, the polymer is not associated with or coordinated with a metal ion. In another variation, the polymer lacks a ligand or functional group that is capable of forming a coordinating complex with metal ions. In one variation of the compound of the formulae A and B, at least one of the group A, B and X is not phenyl. In another variation, at least one of the group A, B and X is not derived from styrene, methyl acrylate, butyl acrylate, benzyl acrylate or a styrene substituted by one —CH$_2$OH.

In another embodiment, there is provided an adhesive composition comprising a polymer of the formula:

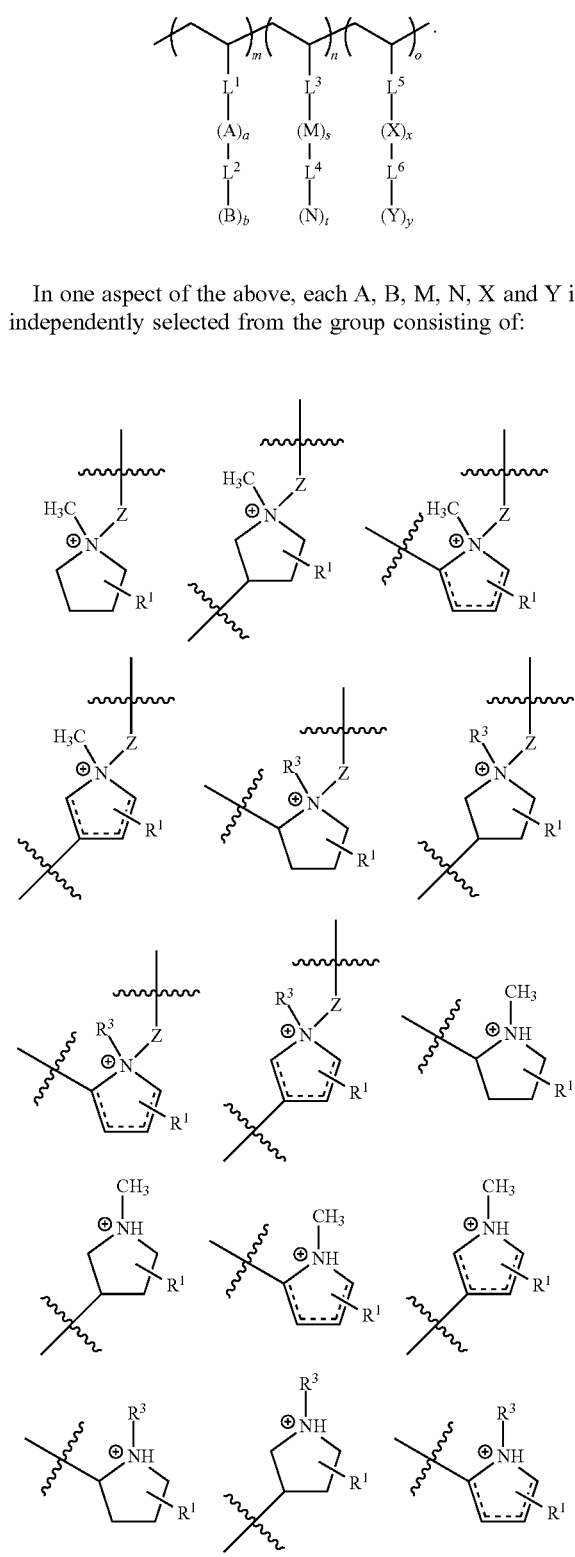

In one aspect of the above, each A, B, M, N, X and Y is independently selected from the group consisting of:

-continued
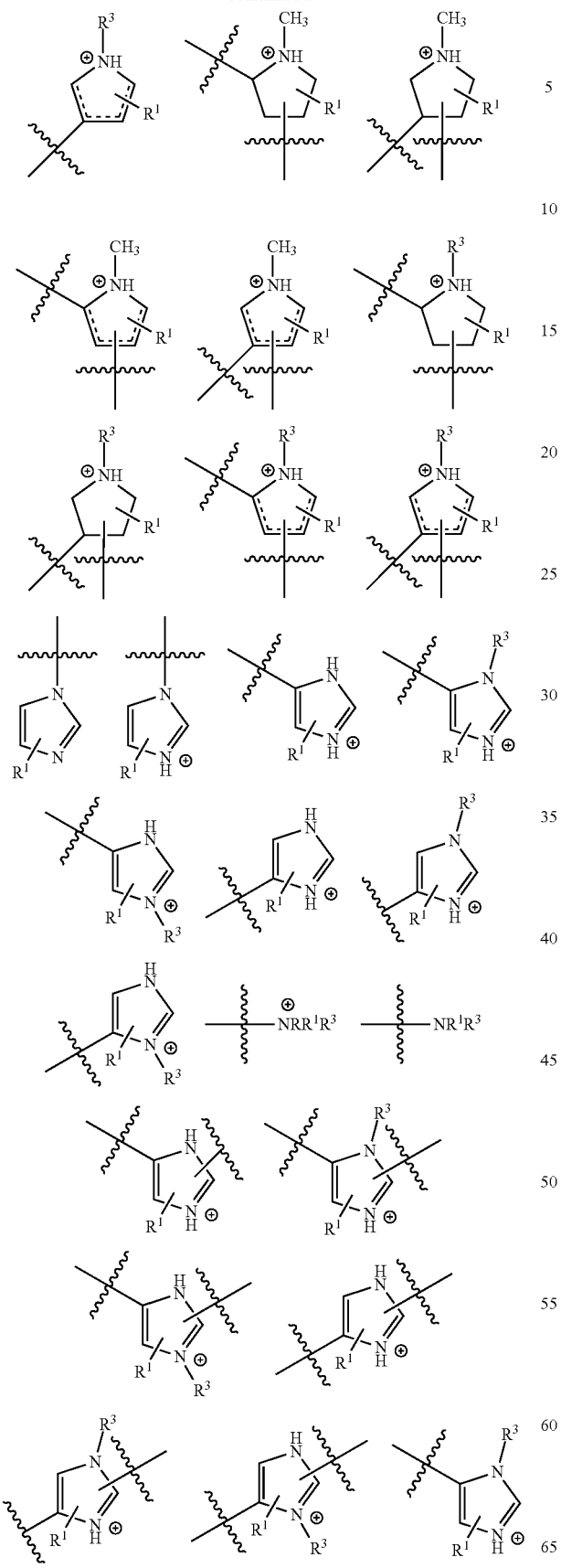
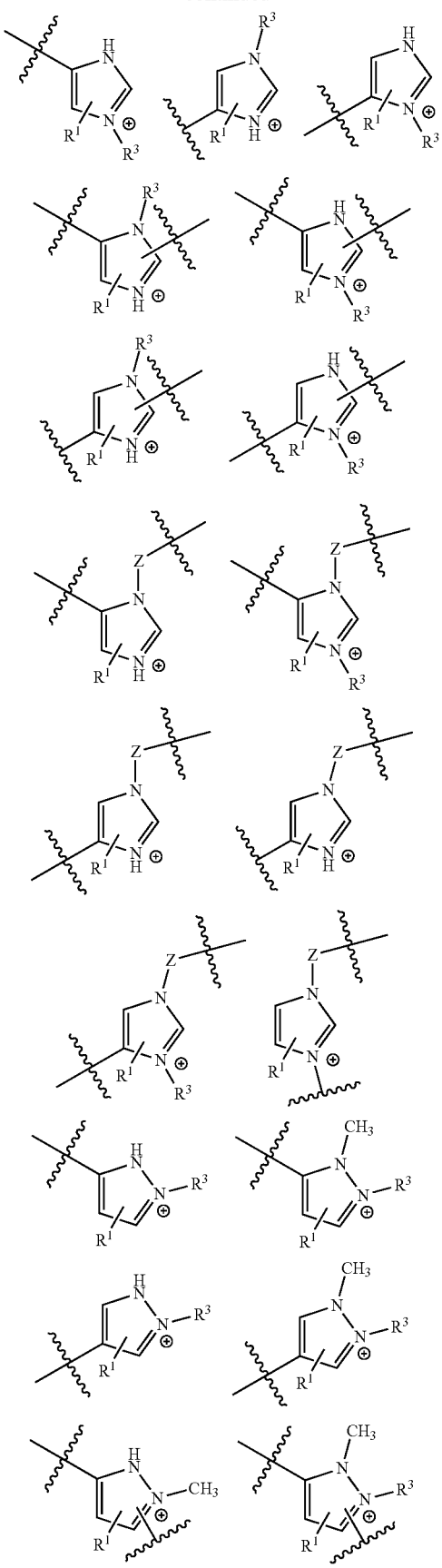

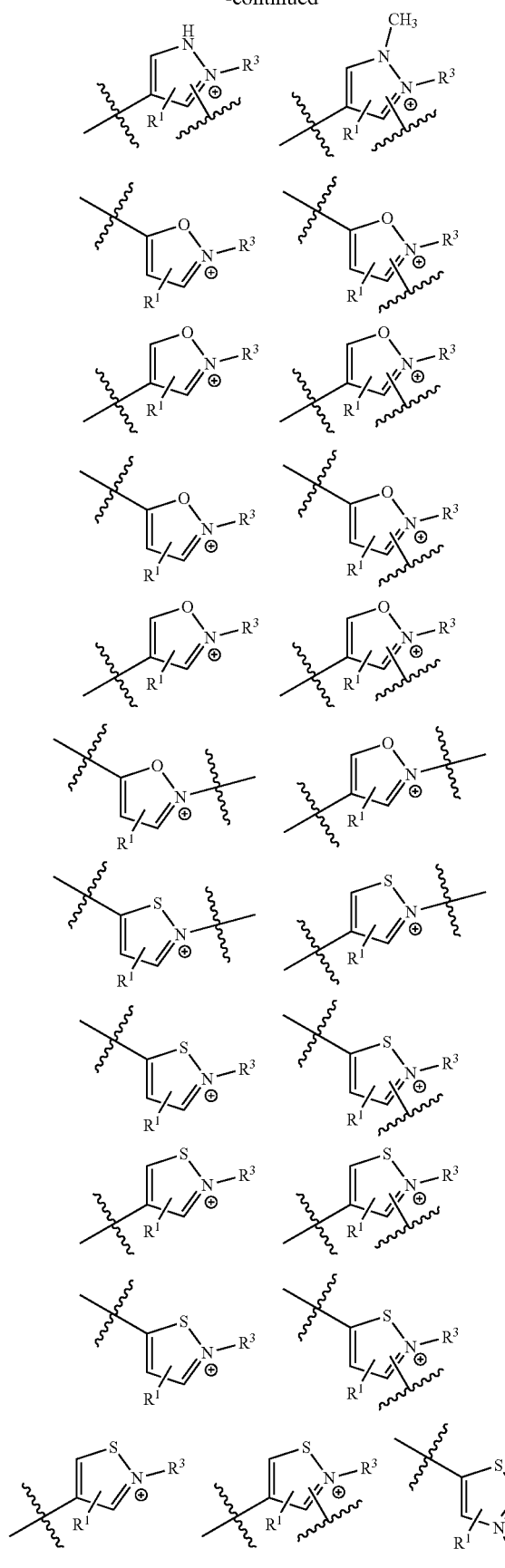
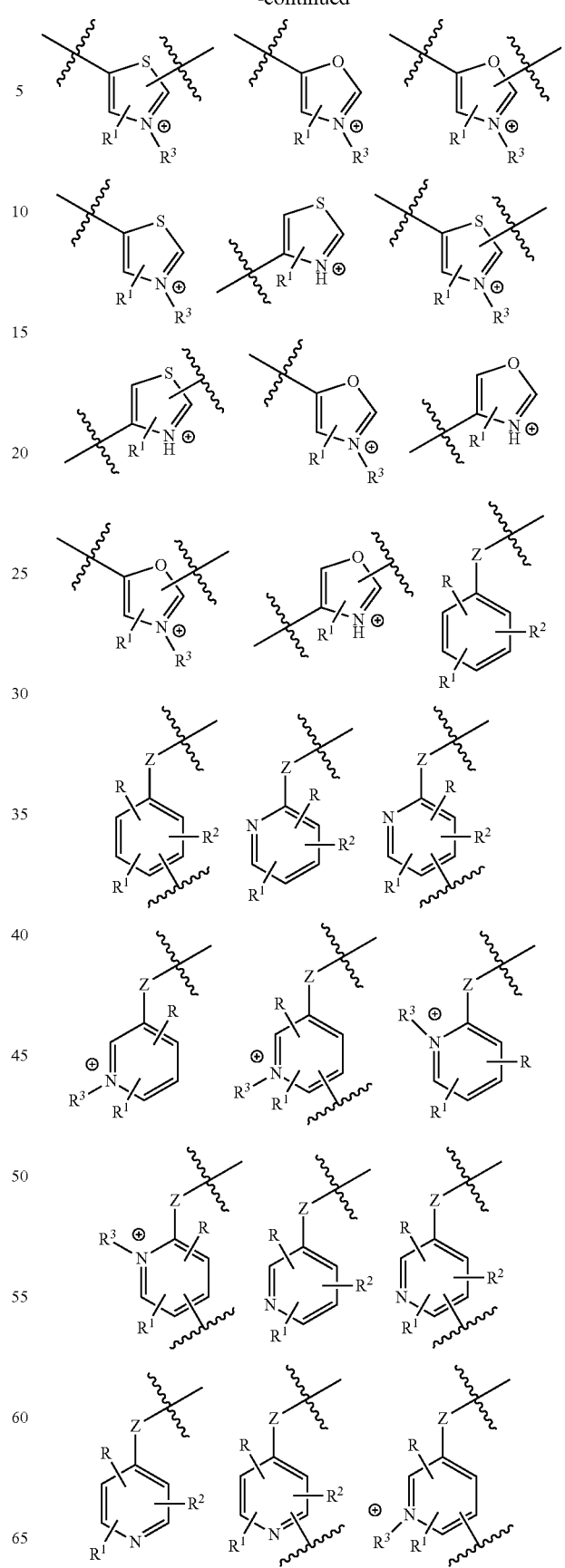

-continued

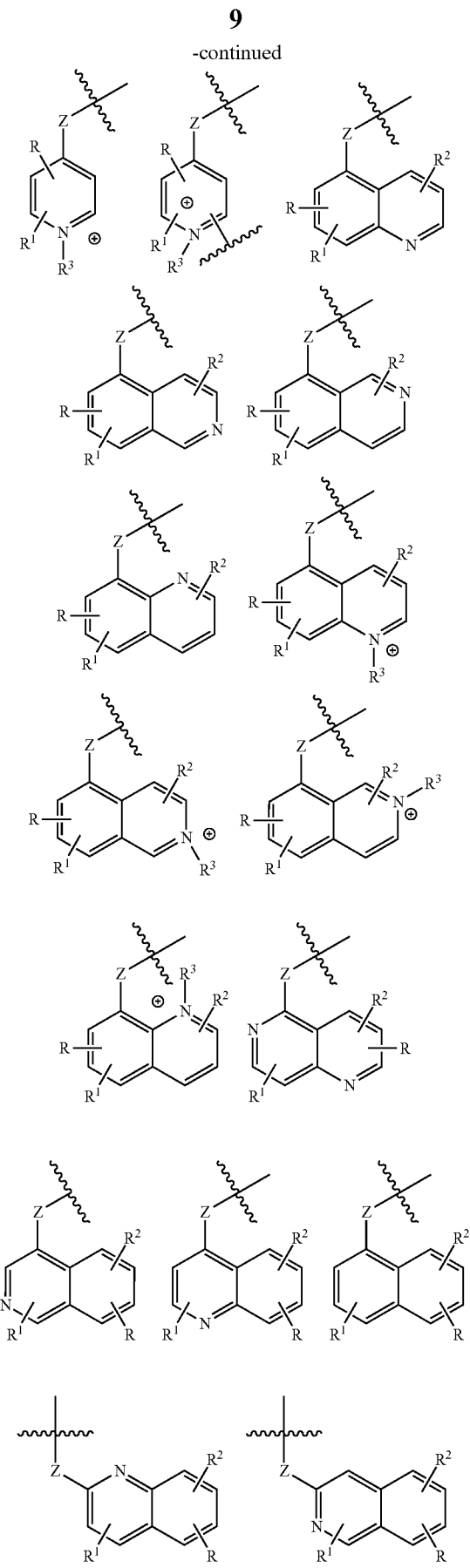

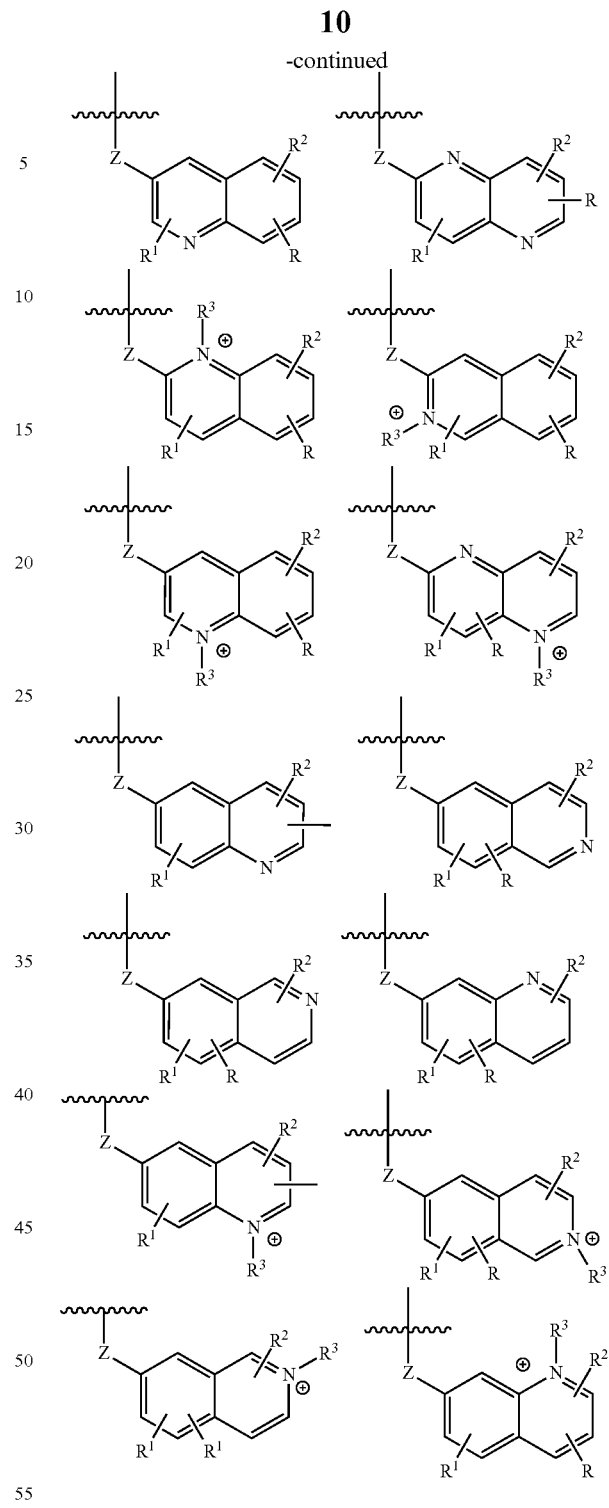

wherein:
each L¹, L², L³, L⁴, L⁵ and L⁶ is independently H, —CH₃, —CH₂—, —O—, —S—, —(CH₂)₁₋₂—, —CH(CH₂—)₂—, —C(O)O—, —C(O)OCH₂—, —CH₂C(O)O—, —CH₂C(O)NH—, —C(O)NHCH₂—, —C(O)NH— and —NR'— where R' is selected from H, —CH₃, —CH₂CH₃ and —CH₂C₆H₅, a bond and —NR'— where R' is selected from H, —CH₃, —CH₂CH₃ and —CH₂C₆H₅ or substituted benzyl;
each R, R¹ and R² is independently H or is selected from the group consisting of F, Cl, Br, I, —OH, —SiH₂OH, —NO₂, —CH₃, —CF₃, a substituted aryl group, —CO₂H, —SO₄H, —SO₃H, —PO₄H₂, —PO₃H₂, —NH₃⁺, —CH₂C₆H₅, -3,4-dihydroxyphenyl, —CH₂-3,4-dihydroxyphenyl, N-succinimidyl, —NR'R" where R' and R" are each independently selected from H, —CH₃, —CH₂CH₃ and —CH₂C₆H₅, and a curable group;

each R³ is independently H or is selected from the group consisting of —CH₃, —CH₂CH₃, a substituted aryl group, —CO₂H, —SO₄H, —SO₃H, —PO₄H₂, —PO₃H₂, —NH₃⁺ and —CH₂C₆H₅, and a curable group; and Z is —(CH₂)ₜ— or —(NH)— where t is 0 or 1.

In another aspect of the above, each of B, N and Y independently comprises an aldehyde derivative, an amine, glycidyl, acrylyl, methacrylyl or a vinyl derivative of the formulae:

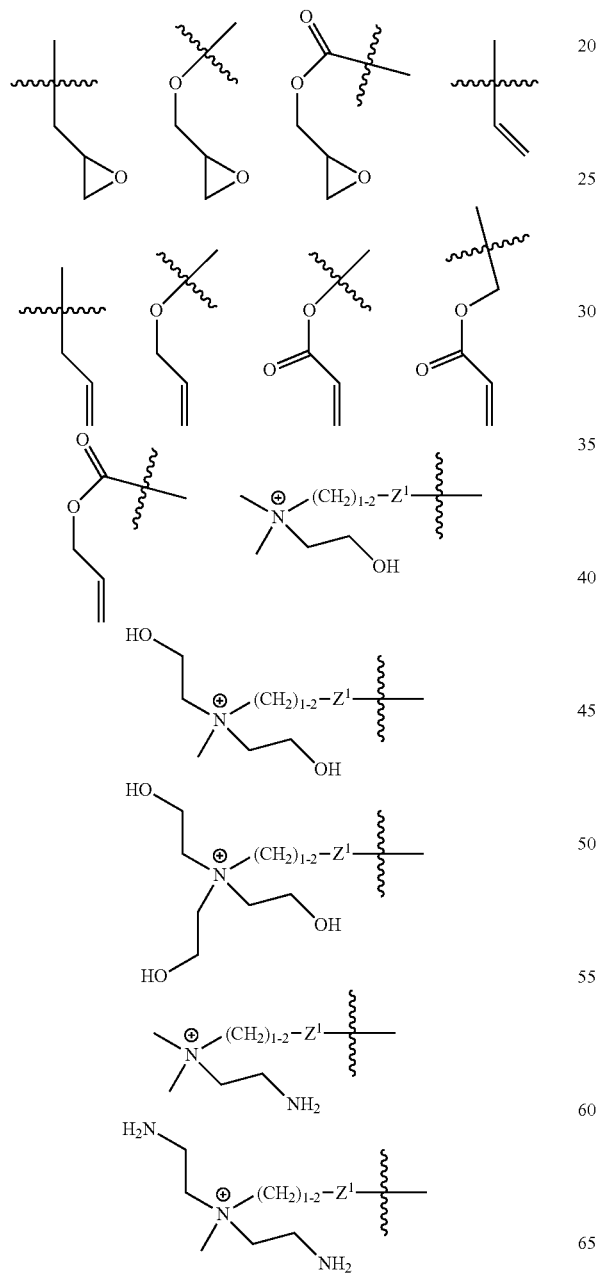

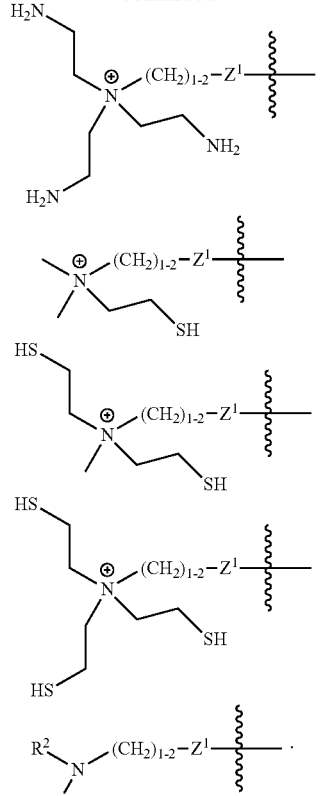

$Z^1$ = O, CH₂, NH, S, or absent

In another aspect of the above polymer, at least one of A, B, M, N, X and Y is independently selected from the group consisting of the formulae:

-L¹-COOH, -L¹-SO₄H, -L¹-SO₃H, -L¹-PO₄H₂, -L¹-PO₃H₂ and L¹-NH₃⁺;

-L³-COOH, -L³-SO₄H, -L³-SO₃H, -L³-PO₄H₂, -L³-PO₃H₂ and L³-NH₃⁺; and

-L⁵-COOH, -L⁵-SO₄H, -L⁵-SO₃H, -L⁵-PO₄H₂, -L⁵-PO₃H₂ and L⁵-NH₃⁺;

wherein each L¹, L³ and L⁵ is independently selected from a bond, —CH₂—, —O—, —S— and —NR'— where R' is selected from H, —CH₃, —CH₂CH₃ and —CH₂C₆H₅ or substituted benzyl.

In another aspect of the above polymer, each of B, N and Y is independently selected from the group consisting of the formulae:

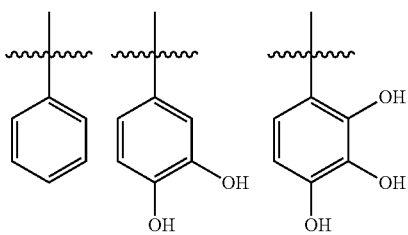

-continued

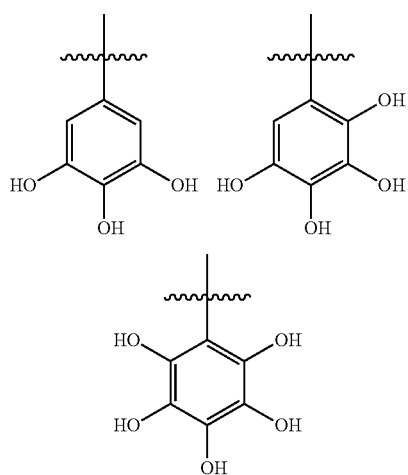

In another aspect of the polymer, at least one of A, M and X is independently selected from the group consisting of the formulae:

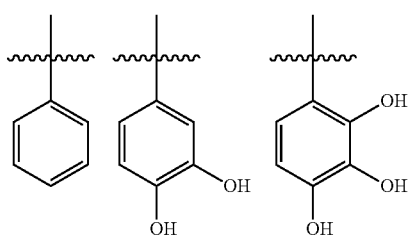

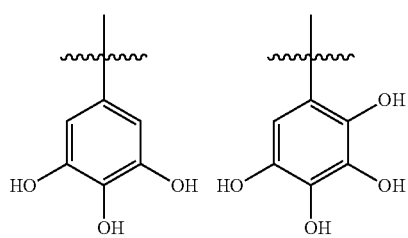

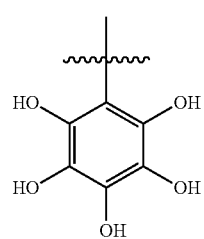

In yet another aspect, B, N and Y are each independently a substituted aryl group. In another aspect of the above, each R, R$^1$, R$^2$ and R$^3$ is independently a substituted aryl group.

In another aspect of the above polymer, the substituted aryl group is selected from the group consisting of:

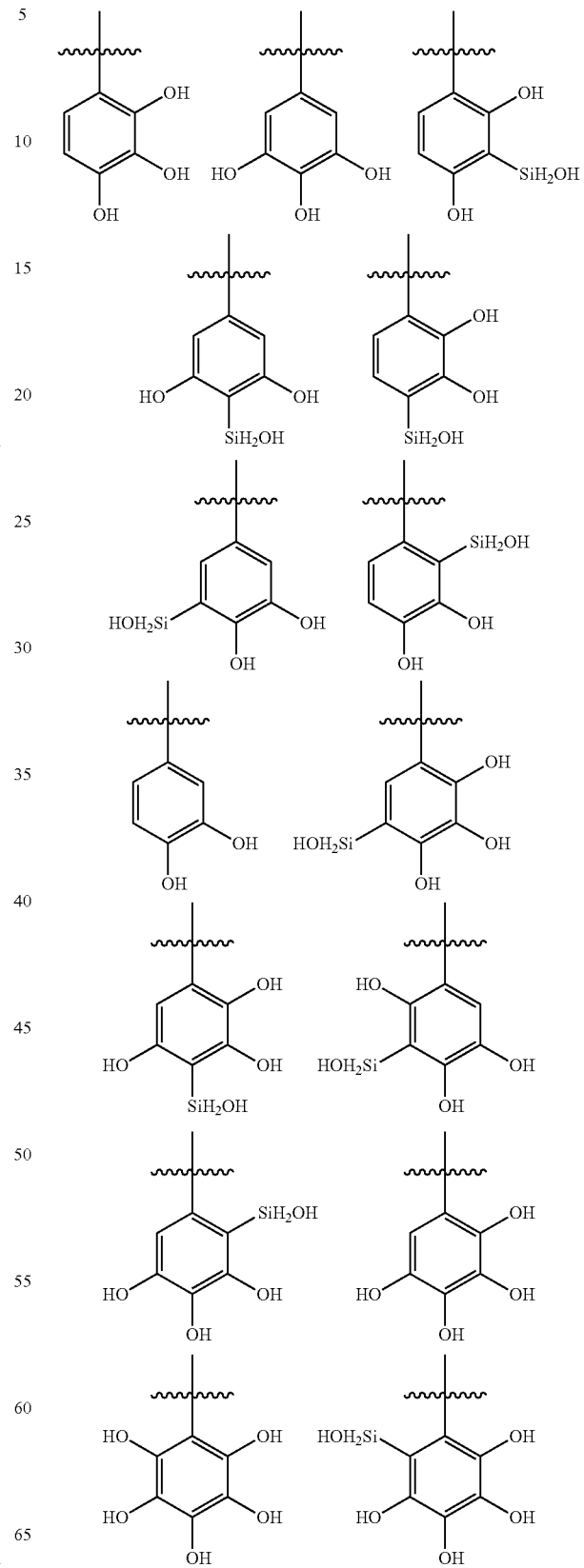

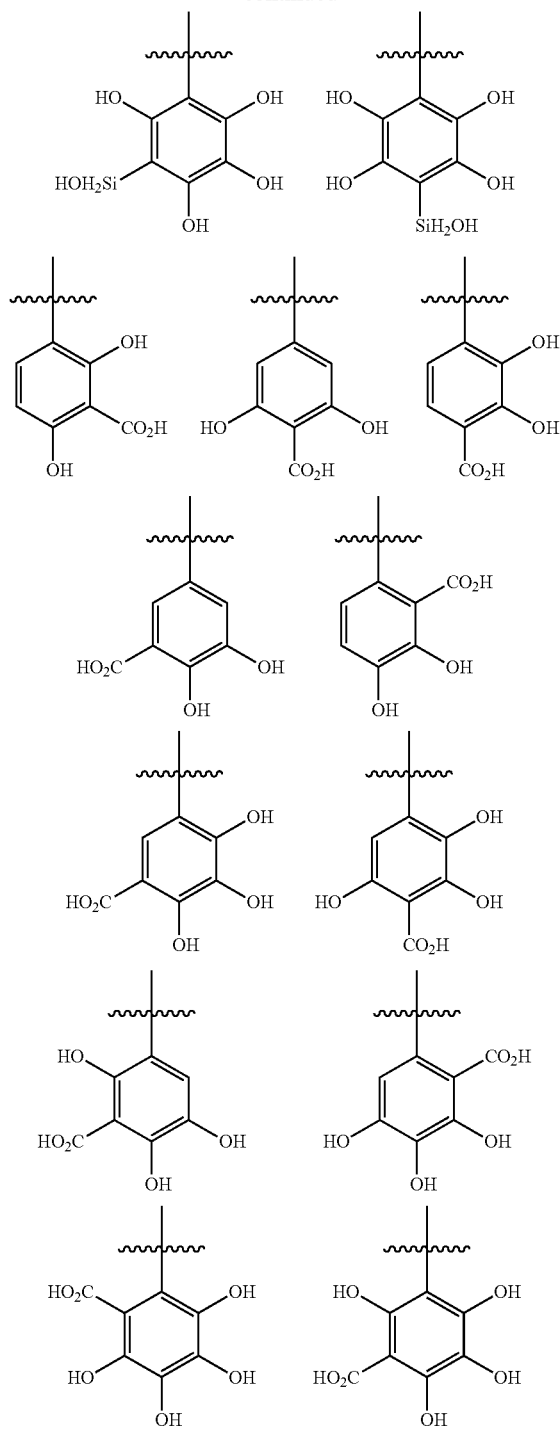
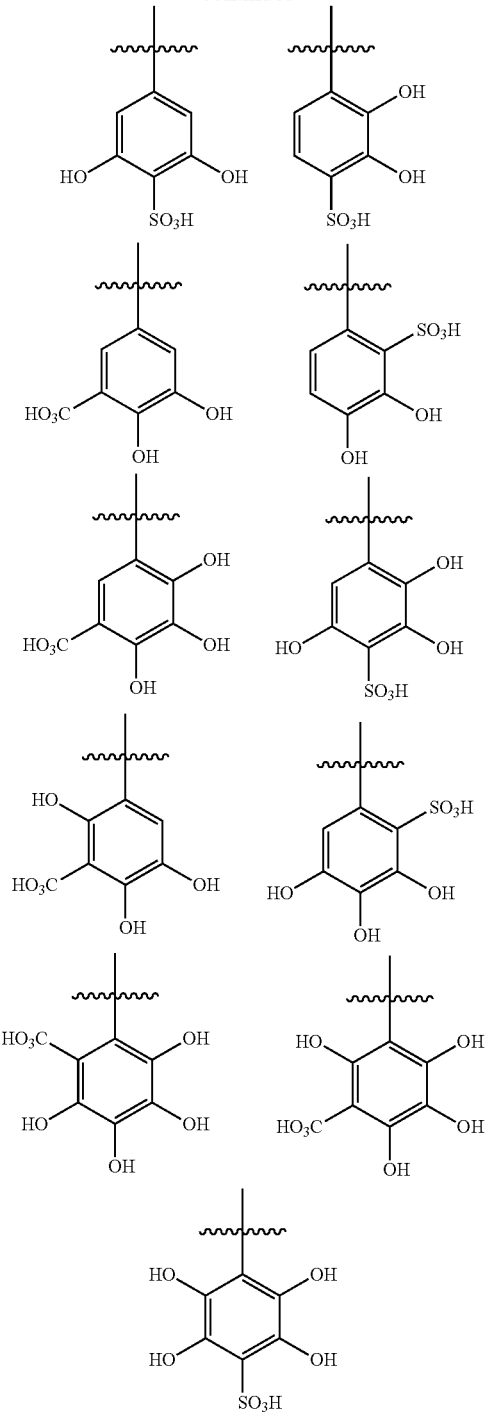
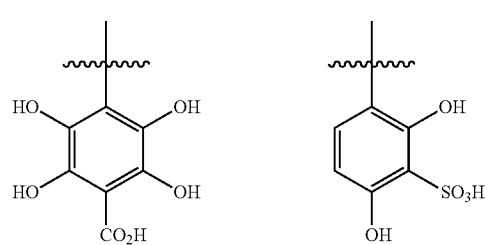

and b, n and y is 1 or 2.

In one variation of the adhesive, each B, N and Y is independently selected from the group consisting of phenyl, 2,3-dihydroxyphenyl, 2,3,4-trihydroxyphenyl, 3,4,5-trihydroxyphenyl, 2,3,4,5-tetrahydroxyphenyl, 2,3,4,5,6-pentahydroxyphenyl, 2,3-dicarboxyphenyl, 2,3,4-tricarboxyphenyl, 3,4,5-tricarboxylphenyl, 2,3,4,5-tetracarboxyphenyl, 2,3,4,5,6-pentacarboxyphenyl, 2,3-disiloxyphenyl, 2,3,4-trisiloxyphenyl, 3,4,5-trisiloxyphenyl, 2,3,4,5-tetrasiloxyphenyl and 2,3,4,5,6-pentasiloxyphenyl.

In another aspect, the adhesive comprises the formulae $B^1$, $B^2$, $B^3$, $B^4$, $B^5$ and $B^6$

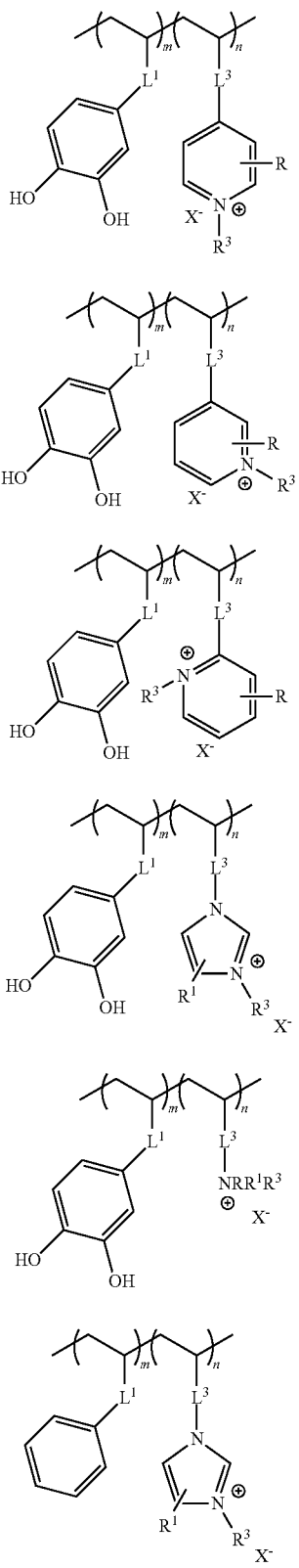

wherein: each m and n is independently 100 to 1,000,000;

each $L^1$ and $L^3$ is independently selected from a bond, —$CH_2$—, —O—, —S—, —C(O)O—, —C(O)OCH$_2$—, —CH$_2$C(O)O—, —CH$_2$C(O)NH—, —C(O)NHCH$_2$—, —C(O)NH— and —NR'— where R' is selected from H, —CH$_3$, —CH$_2$CH$_3$ and —CH$_2$C$_6$H$_5$ or substituted benzyl;

each R and $R^1$ is independently H or is selected from the group consisting of F, Cl, Br, I, —CF$_3$, —OH, —SiH$_2$OH, —NO$_2$, —CH$_3$, —CO$_2$H, —SO$_4$H, —SO$_3$H, —PO$_4$H$_2$, —PO$_3$H$_2$, —NH$_3^+$, —CH$_2$C$_6$H$_5$, -3,4-dihydroxyphenyl, —CH$_2$-3,4-dihydroxyphenyl, —NR'R" where R' and R" are each independently selected from H, —CH$_3$, —CH$_2$CH$_3$, —CH$_2$C$_6$H$_5$ or substituted benzyl, and a curable group;

each $R^3$ is independently H or is selected from the group consisting of —CH$_3$, —CH$_2$CH$_3$, —CO$_2$H, —SO$_4$H, —SO$_3$H, —PO$_4$H$_2$, —PO$_3$H$_2$, —NH$_3^+$, —CH$_2$C$_6$H$_5$ and a curable group; and each $X^-$ is independently a counter anion selected from the group Cl$^-$, Br$^-$, I$^-$, —SO$_4^{-2}$ and —PO$_4^{-3}$.

As depicted in this application, a group represented by the structure $B^3$, for example,

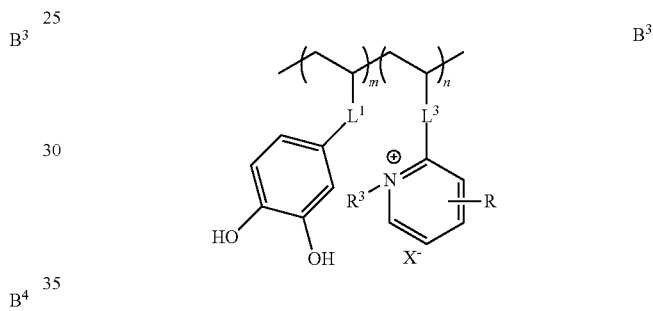

where the substituent —R is attached between 2 carbon atoms on the pyridinium ring means that —R may be attached at any available position on the pyridinium ring, such as the 3-, 4-, 5- or -6 position.

In another aspect, the adhesive comprises the formulae $C^1$, $C^2$, $C^3$, $C^4$, $C^5$ and $C^6$:

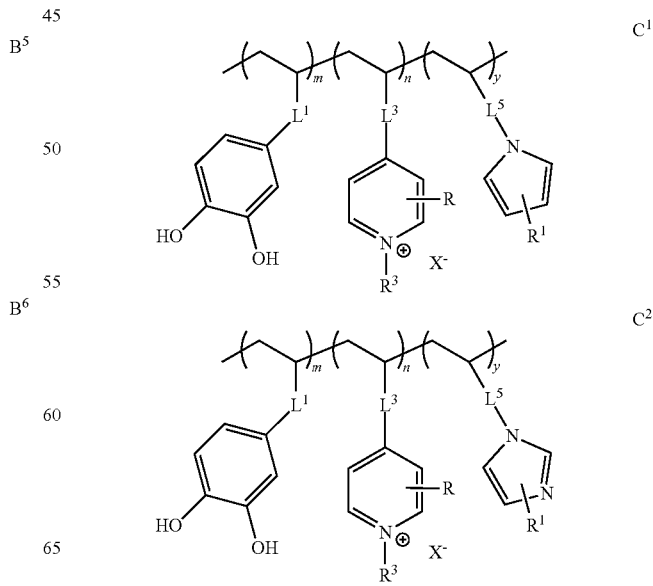

-continued

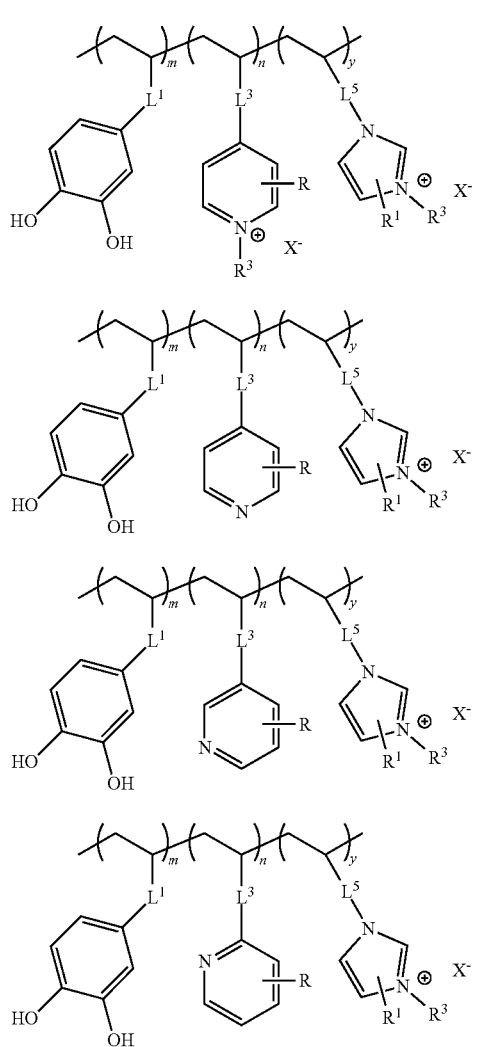

wherein each m, n and y is independently 100 to 1,000,000;

each $L^1$, $L^3$ and $L^5$ is independently selected from —CH$_2$—, —O—, —S—, —(CH$_2$)$_{1-2}$—, —CH(CH$_2$-)$_2$, —C(O)O—, —C(O)OCH$_2$—, —CH$_2$C(O)O—, —CH$_2$C(O)NH—, —C(O)NHCH$_2$—, —C(O)NH— and —NR'— where R' is selected from H, —CH$_3$, —CH$_2$CH$_3$ and —CH$_2$C$_6$H$_5$ or substituted benzyl, or a bond;

each R and $R^1$ is independently H or is selected from the group consisting of F, Cl, Br, I, —OH, —SiH$_2$OH, —NO$_2$, —CH$_3$, —CO$_2$H, —SO$_4$H, —SO$_3$H, —PO$_4$H$_2$, —PO$_3$H$_2$, —NH$_3^+$, —CH$_2$C$_6$H$_5$, -3,4-dihydroxyphenyl, —CH$_2$-3,4-dihydroxyphenyl and —NR'R" where R' and R" are each independently selected from H, —CH$_3$, —CH$_2$CH$_3$ and —CH$_2$C$_6$H$_5$ or substituted benzyl;

each $R^3$ is independently H or is selected from the group consisting of —CH$_3$, —CH$_2$CH$_3$, —CO$_2$H, —SO$_4$H, —SO$_3$H, —PO$_4$H$_2$, —PO$_3$H$_2$, —NH$_3^+$ and —CH$_2$C$_6$H$_5$; and each X$^-$ is independently a counter anion selected from the group consisting of Cl$^-$, Br$^-$, I$^-$, —SO$_4^{-2}$ and —PO$_4^{-3}$.

In another aspect of the above adhesive, B, N and Y are each independently a substituted aryl group. In another aspect of the above adhesive, the substituted aryl group is selected from the group consisting of:

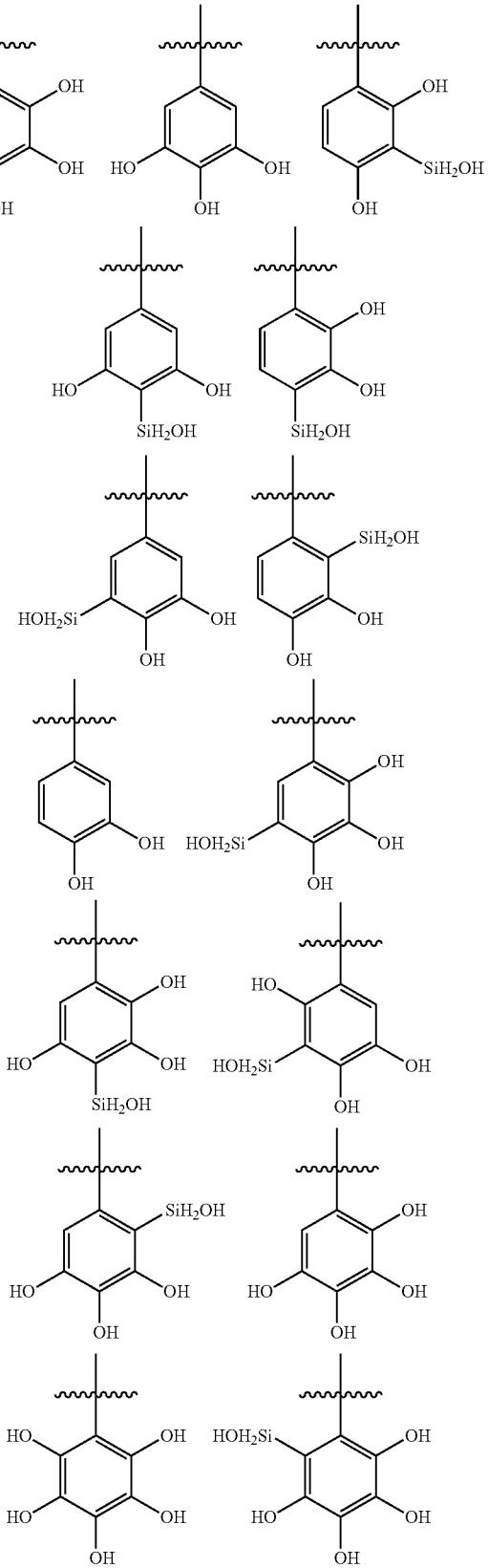

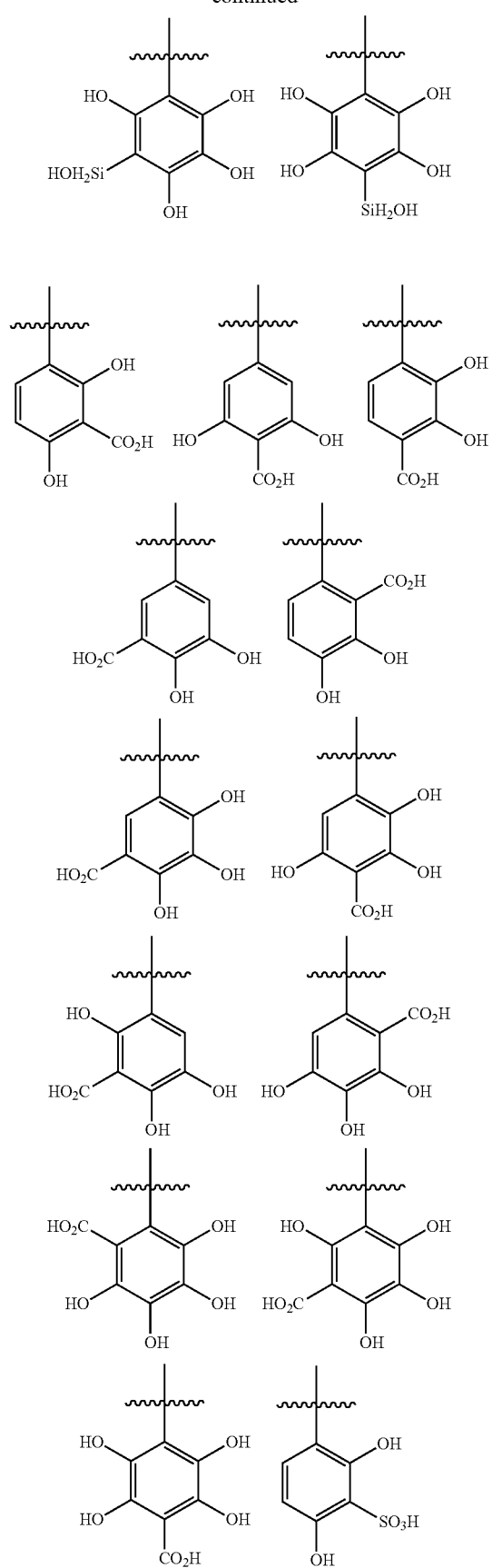
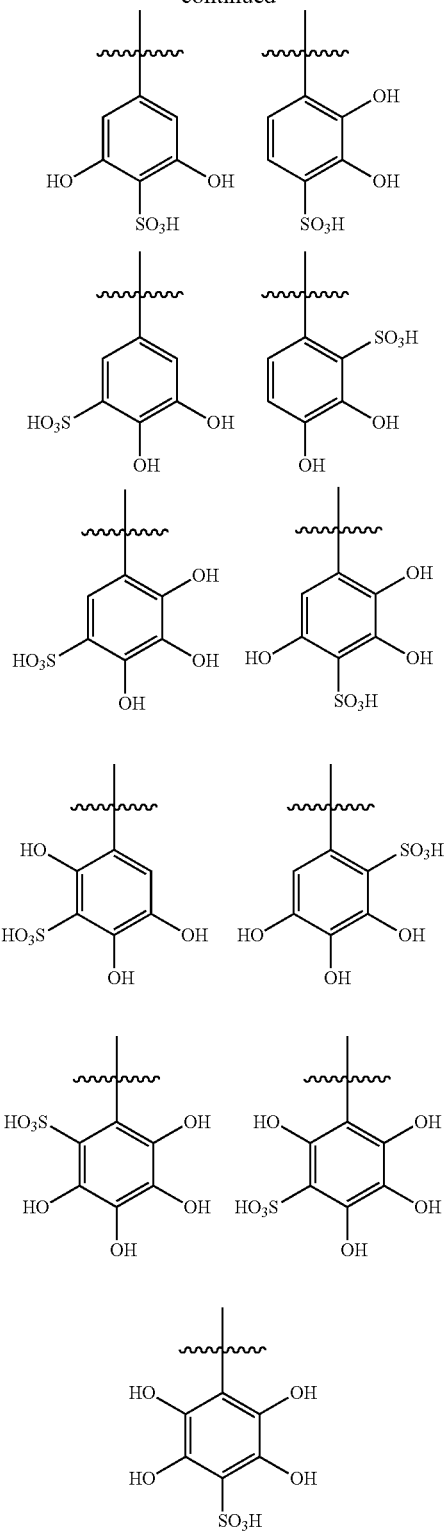
and b, n and y is 1 or 2.
In one variation of the above compounds, R, $R^1$, $R^2$ and $R^3$ are not H. In one variation of the above, b is 0. In another variation, n is 0. In another variation, b and n are both 0. In another variation, b is 1 and n is 0. In another variation, b is 1 and n is 1. In another variation;

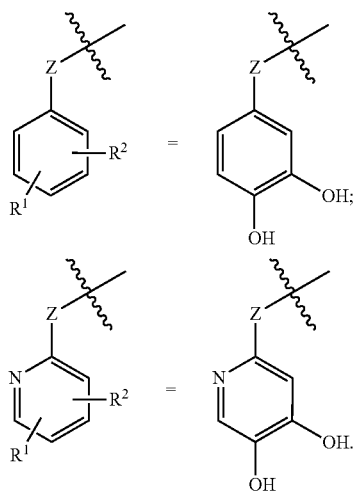

In another aspect of the adhesive, the curable group is a photocurable group, a photopolymerizable group, a thermal curable group and a solvent curable group. In one aspect of the photocurable group, the group may be cured through UV radiation, or by the use of dye-based photoinitiator systems using UV or visible light, thermally induced curing or solvent based curing methods. The photoinitiation may be performed using free radical method or by ionic method. In one variation, the photoinitiator may include doping the polymer, such as the polymer applied to the surface(s) with a small amount of photoinitiator, followed by selective radiation of light, that results in a highly cross-linked polymer-adhesive.

In one variation, the curing adhesive with a curable group, is an epoxide (or a glycidyl group or oxirane group), polyepoxide or epoxy resin that are reactive prepolymers and polymers comprising an epoxide group. Epoxy groups or epoxy resins may be reacted or cross-linked either with themselves by way of catalytic homopolymerization, or with other co-reactants such as amines, polyfunctional amines, acids, acid anhydrides, phenols, alcohols and thiols.

In one variation, the curable group is selected from the group consisting of epoxides, cyanate esters and acrylamido-2-methylpropane sulfonic acid (AMPS) derivative (such as 2-acrylamido-2-methylpropane sulfonic acid). In another variation, the free radical curable group comprises a monomeric organofunctional silanes for polymerization may comprise acrylatoalkylalkoxysilanes, methacrylatoalkylalkoxysilanes or vinyl alkoxysilane monomers, including 3-methacryloxypropyltri-iso-propoxysilane, 3-methacryloxypropyltri-iso-butoxysilane, 3-methacryloxypropyltrioctoxysilane, vinyl tri-iso-butoxysilane, vinyl tri-n-decoxysilane and vinyl tri-tert-butoxysilane, maleate functional silanes and 3-mercaptopropyl tri-iso-butoxysilane. In another variation, the radical curable group is a monomeric organofunctional silane, such as 3-aminopropyltri-iso-propoxy silane, N-(2-aminoethyl)-3-aminopropyidi-iso-butoxy silane, 4-mercaptobutyl dimethyloctyloxysilane, 3-isocyanatopropyltri-sec-butoxysilane and 3-glycidoxypropylmethyl dipentoxysilane. Other curable polymers or curable groups include polyurethanes, epoxies, polyesters, vinyl esters, polyureas and polyamides. See, for example, U.S. Pat. No. 6,069,200.

In another embodiment, the present application discloses a method for sealing a first object having a surface to a second object having surface in a moist or wet environment, the method comprising:
1) applying an adhesive to the surface of the first object;
2) contacting the surface of the first object comprising the adhesive with the surface of the second object for a sufficient period of time until the first and second object forms a seal;
wherein the adhesive is an adhesive composition comprising a polymer of the formula A, B or C:

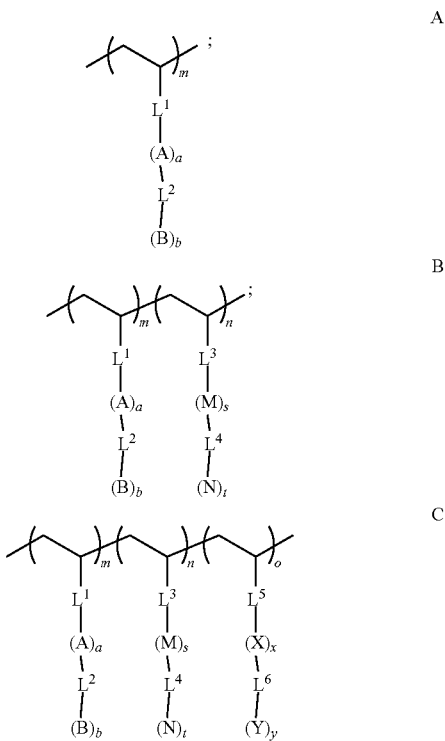

wherein: each m, n and o is independently 100 to 1,000,000;
each a, b, s, t, x and y is independently 0, 1 or 2;
each $L^1$, $L^2$, $L^3$, $L^4$, $L^5$ and $L^6$ is independently absent or is independently selected from —$CH_2$—, —O—, —S—, —$(CH_2)_{1-2}$—, —$CH(CH_2—)_2$, —$C(O)O$—, —$C(O)OCH_2$—, —$CH_2C(O)O$—, —$CH_2C(O)NH$—, —$C(O)NHCH_2$—, —$C(O)NH$— and —NR'— where R' is selected from H, —$CH_3$, —$CH_2CH_3$ and —$CH_2C_6H_5$ or substituted benzyl, or a bond;
each A, B, M, N, X and Y is independently absent or is independently selected from the group consisting of an aryl, substituted aryl, heteroaryl, substituted heteroaryl, heteroarylammonium $X^-$ and substituted heteroarylammonium $X^-$, wherein each $X^-$ is independently a counter anion selected from $Cl^-$, $Br^-$, $I^-$, —$SO_4^{-2}$ and —$PO_4^{-3}$; provided that not all of $L^1$, $L^2$, $L^3$, $L^4$, $L^5$ and $L^6$ and A, B, M, N, X and Y are absent. In one variation of the above method, it is provided that for Formula A, only one of A, B is a heteroarylammonium $X^-$ or a substituted heteroarylammonium $X^-$; and provided that when $L^1$ is —$(CH_2)_{1-2}$— or a bond, then the group -$(A)_a$-$L^2$-$(B)_b$ is not a group selected from -heteroarylammonium ($X^-$)-$L^2$-dihydroxy-phenyl, a substituted or unsubstituted imidazole and a substituted or unsubstituted imidazolinium ($X^-$).

In one variation of the method, the adhesive is a compound or a polymer as disclosed herein. In another aspect of the method, the adhesive comprises of the formulae $A^1$, $A^2$, $A^3$, $A^4$, $A^5$, $A^6$, $A^7$, $A^8$, $A^9$, $A^{10}$, $A^{11}$ and $A^{12}$:
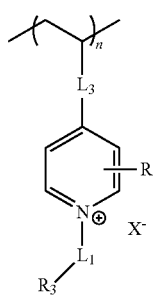
$A^1$
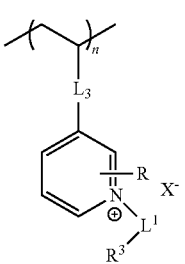
$A^2$
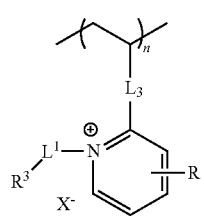
$A^3$
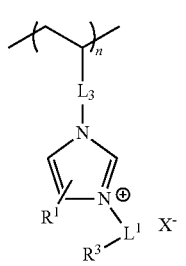
$A^4$
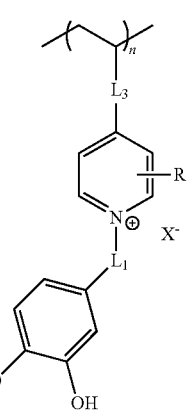
$A^5$
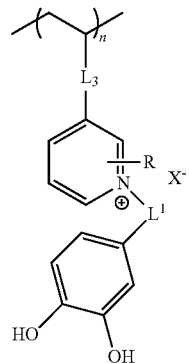
$A^6$
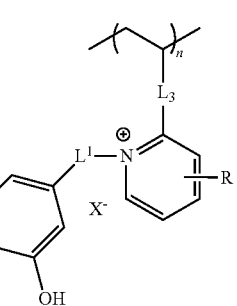
$A^7$
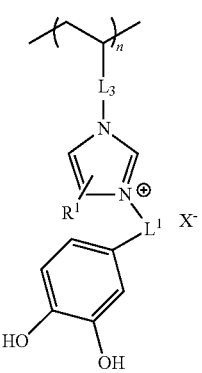
$A^8$
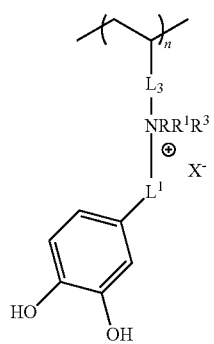
$A^{14}$

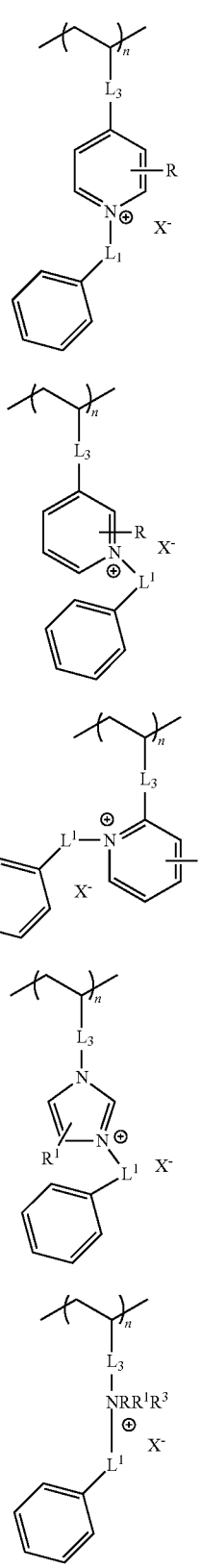

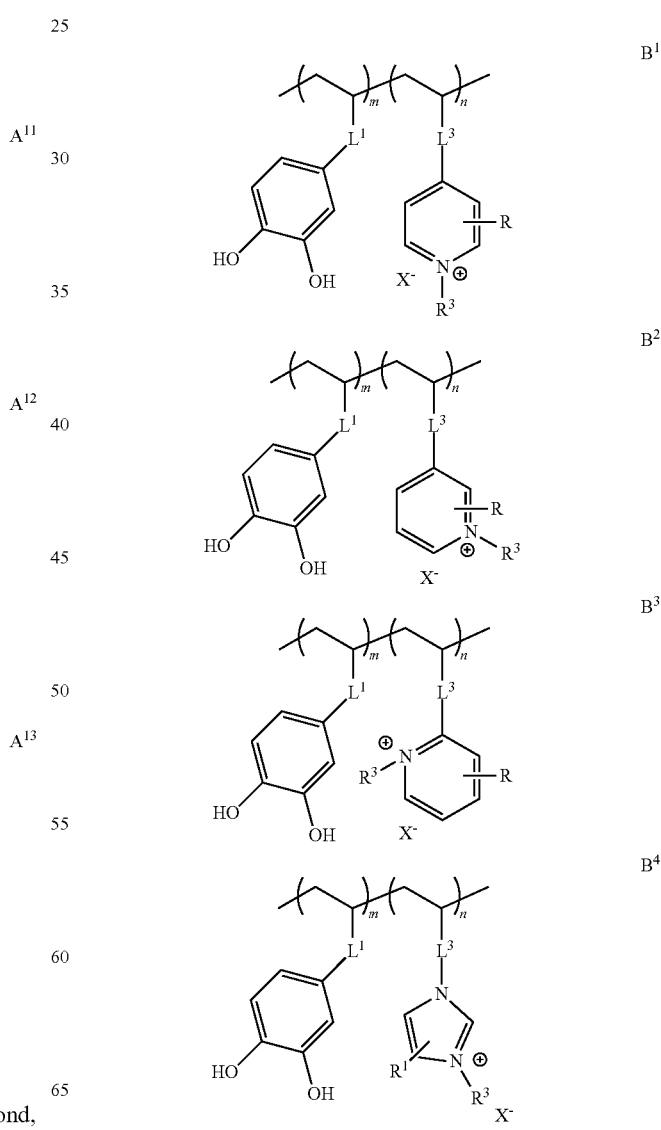

—CH₂C(O)O—, —CH₂C(O)NH—, —C(O)NHCH₂—, —C(O)NH— and —NR'— where R' is selected from H, —CH₃, —CH₂CH₃ and —CH₂C₆H₅ or substituted benzyl;

each R and $R^1$ is independently H or is selected from the group consisting of F, Cl, Br, I, —OH, —SiH₂OH, —NO₂, —CH₃, —CO₂H, —SO₄H, —SO₃H, —PO₄H₂, —PO₃H₂, —NH₃⁺, —CH₂C₆H₅, -3,4-dihydroxyphenyl, a curable group, —CH₂-3,4-dihydroxyphenyl, —NR'R" where R' and R" are each independently selected from H, —CH₃, —CH₂CH₃ and —CH₂C₆H₅ or substituted benzyl;

each $R^3$ is independently H or is selected from the group consisting of —CH₃, —CH₂CH₃, a curable group and —CH₂C₆H₅ where the C₆H₅ group is optionally substituted with 1 substituent selected from the group consisting of halogen (—F, —Cl, —Br— or —I), —OH, —SH, —SiH₂OH, —NH₂, —NO₂, —CO₂H, —SO₄H, —SO₃H, —PO₄H₂, —PO₃H₂, —NH₃⁺, —CH₃, —CF₃, —OCH₃ and —OCF₃; and each X⁻ is independently a counter anion selected from Cl⁻, Br⁻, I⁻, —SO₄⁻², —PO₄⁻³ and CH₃CO₂⁻.

In one aspect of the method, the adhesive comprises of the formulae $B^1$, $B^2$, $B^3$, $B^4$, $B^5$ and $B^6$:

wherein: each n is independently 100 to 1,000,000;
each $L^1$ and $L^3$ is independently selected from a bond, —CH₂—, —O—, —S—, —C(O)O—, —C(O)OCH₂—,

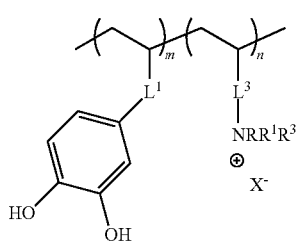
B⁵

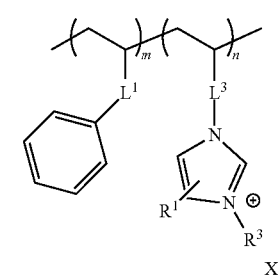
B⁶ wherein: each m and n is independently 100 to 1,000,000;

each L¹ and L³ is independently selected from a bond, —CH₂—, —O—, —S—, —C(O)O—, —C(O)OCH₂—, —CH₂C(O)O—, —CH₂C(O)NH—, —C(O)NHCH₂—, —C(O)NH— and —NR'— where R' is selected from H, —CH₃, —CH₂CH₃ and —CH₂C₆H₅ or substituted benzyl;

each R and R¹ is independently H or is selected from the group consisting of F, Cl, Br, I, —OH, —SiH₂OH, —NO₂, —CO₂H, —SO₄H, —SO₃H, —PO₄H₂, —PO₃H₂, —NH₃⁺, —CH₃, —CH₂C₆H₅, -3,4-dihydroxyphenyl, —CH₂-3,4-dihydroxyphenyl, a curable group, —NR'R" where R' and R" are each independently selected from H, —CH₃, —CH₂CH₃ and —CH₂C₆H₅ or substituted benzyl;

each R³ is independently H or is selected from the group consisting of —CO₂H, —SO₄H, —SO₃H, —PO₄H₂, —PO₃H₂, —NH₃⁺, —CH₃, —CH₂CH₃, —CH₂C₆H₅ or substituted benzyl, and a curable group; and each X⁻ is independently a counter anion selected from Cl⁻, Br⁻, I⁻, —SO₄⁻², —PO₄⁻³ and CH₃CO₂—.

In another aspect of the method, the adhesive comprises the formulae C¹, C², C³, C⁴, C⁵ and C⁶:

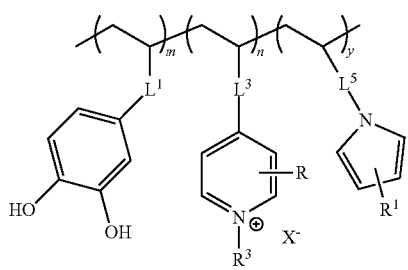
C¹

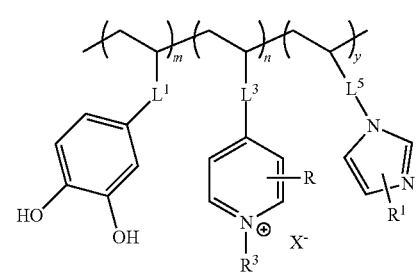
C²

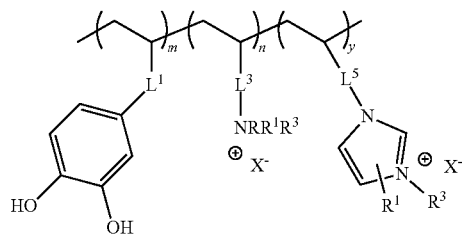
C³

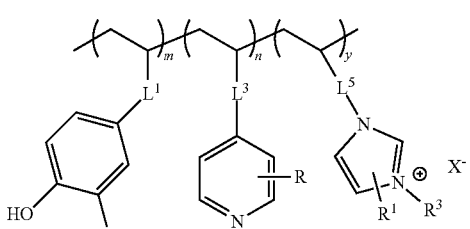
C⁴

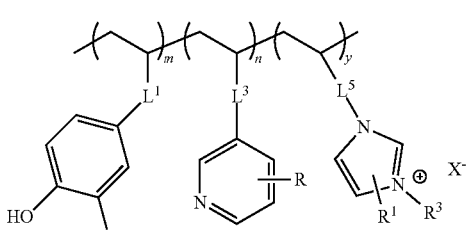
C⁵

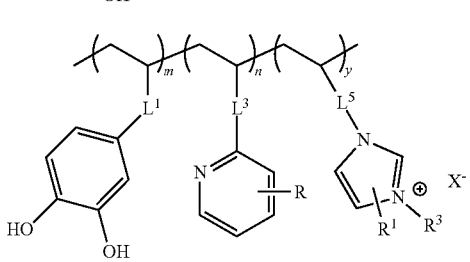
C⁶ wherein: each m, n and o is independently 100 to 1,000,000;

each L¹, L³ and L⁵ is independently selected from a bond, —CH₂—, —O—, —S—, —C(O)O—, —C(O)OCH₂—, —CH₂C(O)O—, —CH₂C(O)NH—, —C(O)NHCH₂—, —C(O)NH— and —NR'— where R' is selected from H, —CH₃, —CH₂CH₃ and —CH₂C₆H₅ or substituted benzyl;

each R and R¹ is independently H or is selected from the group consisting of F, Cl, Br, I, —OH, —SiH₂OH, —NO₂, —CO₂H, —SO₄H, —SO₃H, —PO₄H₂, —PO₃H₂, —NH₃⁺, —CH₃, —CH₂C₆H₅, -3,4-dihydroxyphenyl, a curable group, —CH₂-3,4-dihydroxyphenyl, —NR'R" where R' and R" are each independently selected from H, —CH₃, —CH₂CH₃ and —CH₂C₆H₅ or substituted benzyl;

each $R^3$ is independently H or is selected from the group consisting of —$CO_2H$, —$SO_4H$, —$HSO_4^-$, —$SO_3H$, —$PO_4H_2$, —$PO_3H_2$, —$NH_3^+$, —$CH_3$, —$CH_2CH_3$, —$CH_2C_6H_5$ or substituted benzyl, or a curable group; and each $X^-$ is independently a counter anion selected from $Cl^-$, $Br^-$, $I^-$, —$SO_4^{-2}$ and —$PO_4^{3-}$.

In another aspect of the method, B, N and Y are each independently an aryl or substituted aryl group. In another aspect of the above method, R, $R^1$, $R^2$ and $R^3$ is independently hydrogen or an aryl or substituted aryl group. In another aspect of the method, at least one of A, B, M, N, X and Y is independently selected from the group consisting of the formulae:

-$L^1$-COOH, -$L^1$-$SO_4H$, -$L^1$-$SO_3H$, -$L^1$-$PO_4H_2$, -$L^1$-$PO_3H_2$ and $L^1$-$NH_3^+$;

-$L^3$-COOH, -$L^3$-$SO_4H$, -$L^3$-$SO_3H$, -$L^3$-$PO_4H_2$, -$L^3$-$PO_3H_2$ and $L^3$-$NH_3^+$; and -$L^5$-COOH, -$L^5$-$SO_4H$, -$L^5$-$SO_3H$, -$L^5$-$PO_4H_2$, -$L^5$-$PO_3H_2$ and $L^5$-$NH_3^+$;

wherein each $L^1$, $L^3$ and $L^5$ is independently selected from a bond, —$CH_2$—, —O—, —S— and —$NR'$— where R' is selected from H, —$CH_3$, —$CH_2CH_3$ and —$CH_2C_6H_5$.

In another aspect of the method, each of B, N and Y independently comprises an amine, glycidyl, acrylyl, methacrylyl, or a vinyl derivative of the formulae:

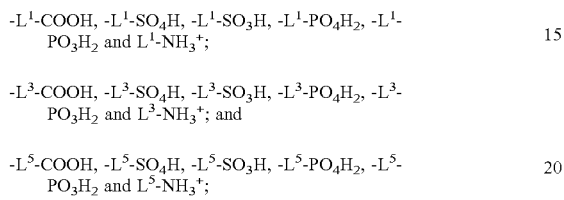

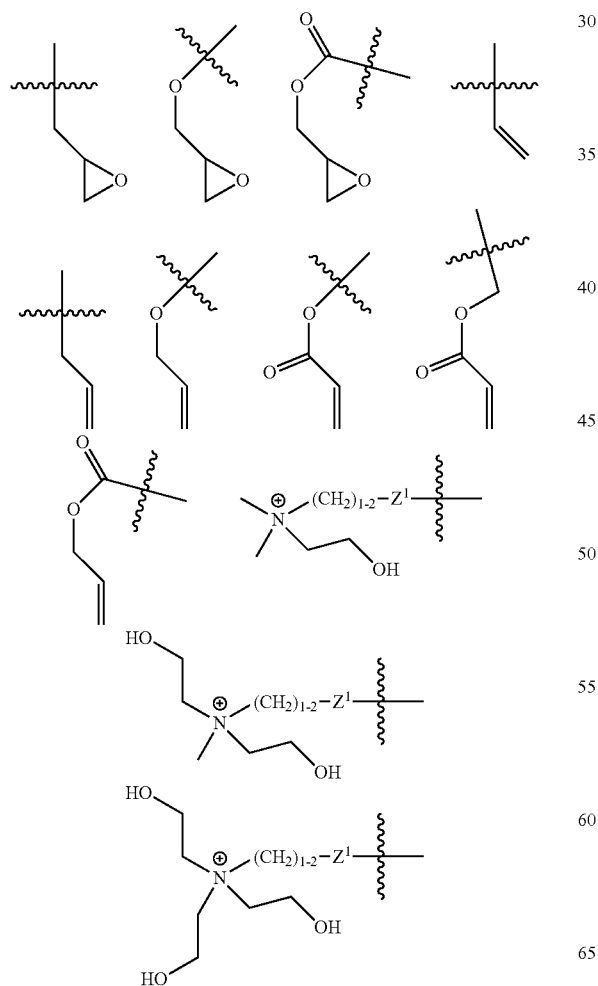

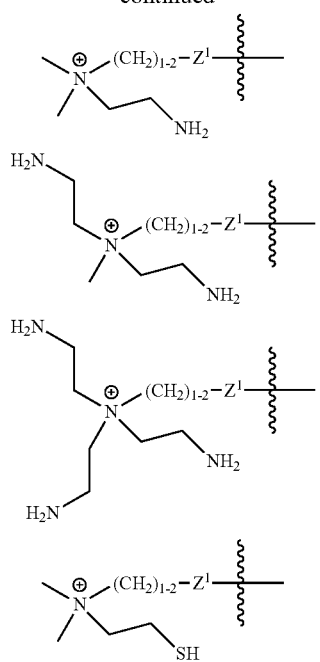

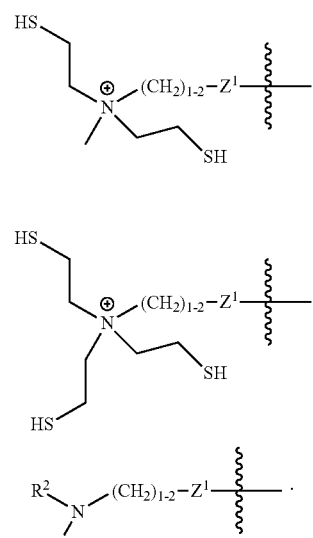

$Z^1$ = O, $CH_2$, NH, S, or absent

In another aspect of the method, each of B, N and Y is independently selected from the group consisting of the formulae:

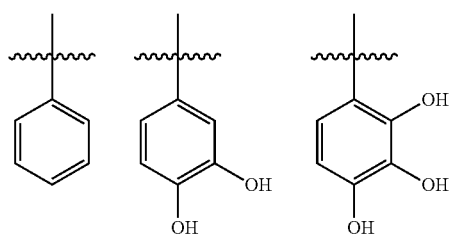

-continued

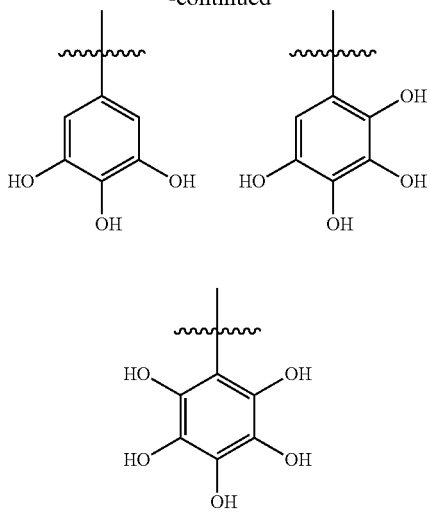

In yet another aspect of the method, at least one of A, M and X is independently selected from the group consisting of the formulae:

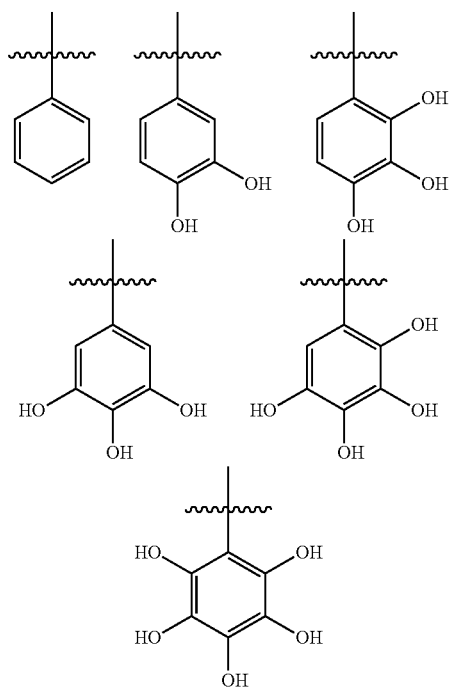

In yet another aspect of the above method, the adhesive is further cured. In one variation of the method for sealing a first object having a surface to a second object having surface in a moist or wet environment, the method comprising polymerizing a first monomer to form a polymer, such as a homopolymer, applying the polymer to the surface of the first object and contact the surface of a second object to the surface of the first object comprising the polymer for a sufficient period of time to seal the first object to the second object. In one variation of the method, the sealing of the first object to the second object is performed in a moist environment. In one variation of the method, the most environment is an aqueous environment. In another variation of the method, the sealing of the first object to the second object is performed in water, in a moist or a wet atmosphere or under water.

In another variation of the method, the adhesive is further cured under standard methods known in the art, such as by heat, light (UV or visible), radiation, electron beams or by adding certain chemical additives. In one variation, the additive may be activated with UV radiation resulting in a UV curing process.

In another aspect of the method, the first object is independently selected from the group consisting of a dermis, skin, tissue, metal, a metal oxide, a mineral, mica, silicon, glass, calcium, enamel, bone, steel, tooth enamel, tooth dentin, hydroxylapatite, kaolin and zirconia; and the second object is selected from the group consisting of a dermis, skin, tissue, metal, a metal oxide, a mineral, mica, silicon, glass, calcium, enamel, bone, steel, tooth enamel, tooth dentin, hydroxylapatite, kaolin and zirconia. In another aspect, the first object and the second object are both dermis tissues or skin. In yet another aspect, the first object is a tissue or dermis and the second object is selected from the group consisting of a metal, a metal oxide, a mineral, mica, silicon, glass, calcium, enamel, bone, steel, tooth enamel, tooth dentin, hydroxylapatite, kaolin and zirconia.

In another aspect of the method, the adhesive process is performed in water. In yet another aspect, the method further comprises the addition of saline or salt, or mixture of salts, to increase the salinity. In another aspect of the method, the metal, metal oxide or oxide is selected from the group consisting of silicate mineral, silica, kaolin, zirconia, aluminum, copper, chrome, chrome-cobalt, titanium, zinc, tin, indium-tin and calcium oxide. In another aspect, the method provides a reusable or reversible low tack pressure sensitive adhesive or low tack adhesive or anti-slippery coating, where the process comprises: (1) dissolving the above noted adhesive in water to form an aqueous solution of the adhesive; (2) diluting the aqueous solution of the adhesive with an alcohol, such as ethanol; (3) adding saturated NaCl aqueous solution to the aqueous ethanolic solution; (4) spraying, applying or coating the aqueous ethanolic solution on a substrate or surface and drying the solution such as by air drying.

In another embodiment, the adhesive is contacted with the surface and employed after polymerization, or the adhesive is further cured, as shown in Schemes A, B and C.

Scheme A

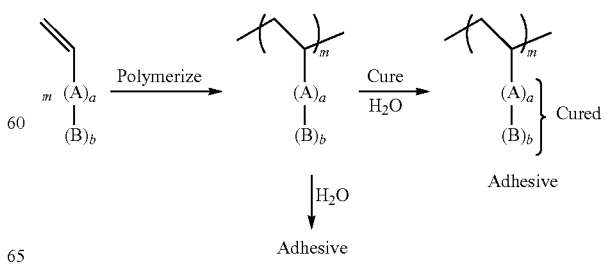

Scheme B

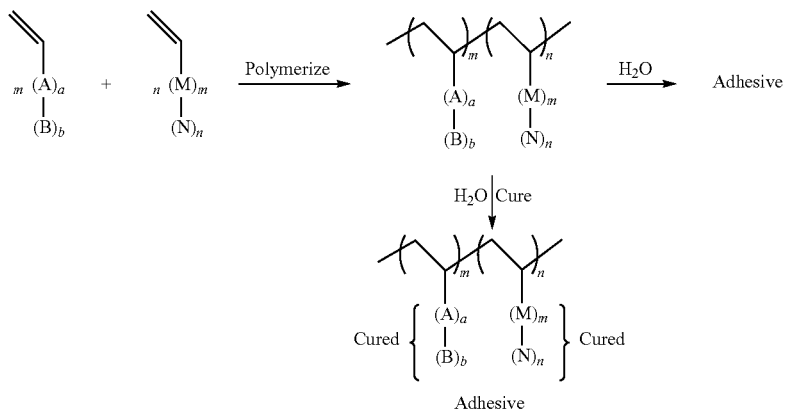

Scheme C

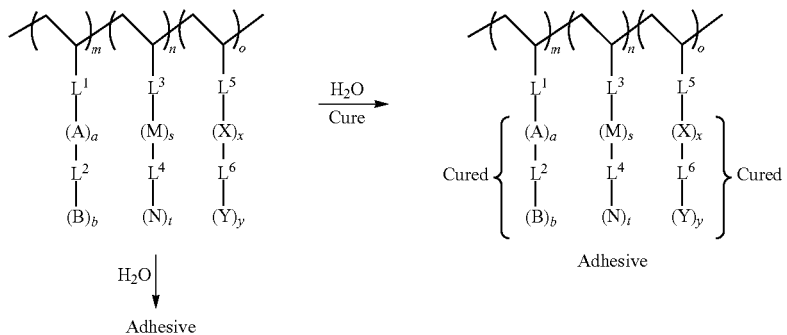

DETAILED DESCRIPTION OF THE INVENTION

Definition

The term "copolymer" means a polymer that is made from two or more different monomers. Examples of such monomers may include ethylene, styrene and acrylonitrile, and their substituted derivatives. For example, two different monomers may be allowed to polymerize in a reaction medium such that a copolymer is formed that contains both residues of the two different monomeric units. In one aspect, the copolymer may be a random copolymer having no definitive sequence of the monomer units. In another aspect, the copolymer may be a regular copolymer with regular alternating sequence of two monomer units. In another aspect, the copolymer may be a block copolymer containing a block of one monomer connected to a block of another monomer.

The total number average molecular weight (Mn, or $M_n$) of the polymers or block polymers or copolymers of the present invention is typically provided in various ranges, of from about 5,000 to 6,000, 6,000 to 8,000, 8,000 to 10,000, 10,000 to 12,000, 28,000 to 30,000, 43,000 to 45,000, 53,000 to 55,000, 58,000 to 60,000, 78,000 to 80,000, 88,000 to 90,000, 97,000 to 100,000, 115,000 to 120,000, 125,000 to 130,000, 135,000 to 140,000, 145,000 to 150,000, 200,000 to 400,000, 400,000 to 500,000, 500,000 to 600,000, 600,000 to 700,000 or about 700,000 to about 1,000,000. The Mn may be determined standard methods employed in the art, such as by using chromatography such as gel permeation chromatography (GPC). The molecular weight of the block copolymer and properties obtained are dependent upon the molecular weight of each of the polymers or polymeric blocks.

The term "cure" or "curing" refers to the hardening or toughening of a polymer material by cross-linking of the polymer chains in the polymer. Such process may be performed by various methods, including by heat, light (UV or visible), radiation, electron beams or by adding certain chemical additives. In certain curing procedures, the additive may be activated with UV radiation resulting in a UV curing process.

The term "homopolymer" means a polymer that are formed by the reaction starting with the same monomer. Homopolymers may include addition polymers that are polymers or macromolecules that are formed by the addition reaction of olefins, acetylenes, aldehydes or other compounds having an unsaturated bond or functional group. Representative homopolymers from monomers include polyethylene from ethylene, poly(vinyl chloride) from vinyl chloride, polyacrylonitrile from acrylonitrile, polystyrene from styrene etc.

The term "monomer" means any substance or molecule that can be converted or made into a polymer. Examples of such monomers may include ethylene, styrene and acrylonitrile. Monomers may also refer to dimers or trimers, if for example, the dimers or trimers can also undergo further polymerization.

"Optionally substituted" means a group, such as an alkyl group, an aryl group, a heteroaryl group, as disclosed herein, may be substituted by one or more substituents selected from halogen (—F, —Cl, —Br— or —I), —OH, —SH, —SiH$_2$OH, —NH$_2$, —NO$_2$, —CH$_3$, —CF$_3$, —OCH$_3$ and —OCF$_3$. For example, an optionally substituted or substituted benzyl group substituted with 1 substituent selected from the group consisting of halogen (—F, —Cl, —Br— or —I), —OH, —SH, —SiH$_2$OH, —NH$_2$, —NO$_2$, —CO$_2$H, —SO$_4$H, —SO$_3$H, —PO$_4$H$_2$, —NH$_3^+$, —CH$_3$, —CF$_3$, —OCH$_3$ and —OCF$_3$.

The term "polymer" means a molecule having a structure that is composed of multiple repeating units, and may refer to a substance or molecule with high molecular weight. Representative of such polymers may include linear polymers comprising a long chain of skeletal atoms to which are attached substituents or substituent groups; branched polymers that may be linear polymers with branches of the same or similar basic structure as the main chain; or cross-linked or network polymers where chemical linkages are present between the chains of the polymers. The polymers or copolymers may be random copolymers, alternating copolymers (e.g., regular alternating A and B monomers), periodic copolymers, statistical copolymers or block copolymers.

The term "random" polymers or copolymers are polymers in which the monomer units are incorporated into the chain wherein there can exist various combinations of ordering including block polymer units where, for example, either the first monomeric unit or second monomeric unit (or third unit, fourth unit etc . . . , as provided herein) or both units may be repeated and are adjacent to one another. "Alternating" first monomeric and second monomeric copolymers are those in which the first monomeric and second monomeric units occur in repeating alternate sequences on the polymer chain in atactic structures (such as isotactic or syndiotactic) or in combinations of the general formula as described herein, wherein x and y are integers from 1 to 10,000. The term "substantially random" as used herein in reference to the first and second monomeric units form a copolymer where the distribution of the monomers or monomeric units of the copolymer may be described by the Bernoulli statistical model or by a first or second order Markovian statistical model, as described by J. C. Randall in Polymer Sequence Determination, Carbon-13 NMR Method. Academic Press NY, 1977, pp. 71-78. The composition (of monomer) distribution of the copolymer can also be determined using $^{13}$C NMR analysis using the methods described in U.S. Pat. Nos. 5,292,845; 5,089,321 and by J. C. Randall, Rev. Macromol. Chem. Phys. C29, pp. 201-317 (1989).

In one embodiment, the present application discloses cationic or amphilic ionic copolymer-containing heterocycles and heterocyclic salts such as pyridines and substituted pyridines, pyridinium salts, substituted pyridinium salts, imidazoles and substituted imidazoles, imidazolium salts and substituted imidazolium salts, epoxides, glycidol derivatives, hydroxy aromatics, hydroxy phenols, polyhydroxy phenols, catechol and substituted catechol monomers which can undergo multiple continuous phase inversion in saline water and may be solidified into an adhesive such as a wet adhesive or wet glue. In another embodiment, there is provided the heterocyclic salts in combination with imidazoles and substituted imidazoles, imidazolium salts and substituted imidazolium salts, epoxides, glycidol derivatives, hydroxy aromatics, hydroxy phenols, polyhydroxy phenols, catechol and substituted catechol monomers. These ionic polymer glues can adhere and adsorb onto surfaces of biological tissues, bones, hydrogels, plastics, metals, ceramics and/or the interfaces between them through a combination of electrostatic, hydrophobic, chelating interactions and hydrogen bonding. Lee, B. P.; Messersmith, P. B.; Israelachvili, J. N.; Waite, J. H., Mussel-Inspired Adhesives and Coatings. *Annu Rev Mater Res,* 2011, 41, 99-132. The bonding strength of these ionic polymer glue can be further enhanced through secondary crosslinking with another functional group, for example, by oxidative crosslinking of a functional group, such as catechol, cationic/anionic/radical polymerization of epoxides, acrylates, methacrylates; coupling/crosslinking of epoxides, arylates, methacrylates, aldehydes, N-succinimidyl group, etc., and at different pH, such as at pH>6 conditions.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited in this specification, including the Background, Detailed Description sections and Examples, are incorporated by reference into this disclosure as if each had been individually incorporated.

Some embodiments in the present application are directed to polymers, such as ionic polymers, that may be used under moist or wet conditions, such as an underwater glue. In one embodiment, the underwater adhesive (wet or bio-glue) is based anionic copolymers containing (1) nitrogen-containing heterocyclic cationic functional residues such as imidazolium groups and pyridinium groups, that are selected from the group consisting of an ammonium, quinolinium, isoquinolinium, phenathridinium, phenanthrolinium, pyrimidinium, benzothoazolinium, benzothiadiazolinium, purinium, pyrazinium or acridinium and (2) coupling residues such as di, tri-, tetra- and penta-hydroxy benzene, polycyclic hydrocarbons (e.g., naphthalene, anthracene, etc.), aryls, heteroaryl, N-succinimidyl, indole and imidazole moieties and their derivatives, that may form bonds, such as hydrogen bonds, covalent bonds and/or attachments on to a material surface and/or form crosslinked networks such as aldehydes, mono-, di- or poly-acrylates and methacrylates, di, tri-, tetra- and penta-hydroxy benzene, polycyclic hydrocarbons (e.g., naphthalene, anthracene, etc.), aryls, heteroaryl, N-succinimidyl, indole and imidazole moieties and their derivatives.

In one variation, the ionic copolymer may be based on any polymer backbones such as polystyrene, polyacrylate, polymethacrylate, polyester, polyether from any vinyl, acrylate and/or methacrylate co-monomers.

In one embodiment, the disclosed polymer contains aryl derivatives, such as benzyl or phenyl derivatives, attached to the pyridine and imidazolium groups through methylene spacer groups. The polymer glue is soluble in water and forms stable aqueous solution. When the aqueous solution of ionic polymer glue is applied to substrates submerged in saline water (salt concentration: 0.1~2 M, pH 1~12 or isotonic), the polymer can undergo liquid-to-solid phase inversions and self-assemble into viscoelastic underwater glue. The glue may coat surfaces (e.g. biological tissues, hydrogel, plastics, metal, glass, ceramics) in saline water, or glue two surfaces or objects together. The strength of the glue can be further enhanced through the oxidative crosslinking of monomers, such as catechol monomers, at pH above 5, 6, 7 or pH 8-9.

In one aspect, x, z are monomer molar ratio of the imidazolium and catechol monomers in the ionic polymer. In some embodiments, the polymer disclosed in the present application may be used as underwater glue or adhesive coating in saline water. The ionic polymer glue of the present application have strong adhesion/cohesion in saline water. The ionic polymer glue may adhere to diverse surfaces and self-assembles into a primer, a coating, a glue or an adhesive layer. In some embodiments, the ionic polymer glue of the present application may be applied onto biological tissues, such as human tissues, including teeth, bones and medical and dental implants, and other materials, including plastics, ceramics and metals.

In some embodiments, the adhesive polymer or ionic polymer glue of the present application may be crosslinked or further cured, as disclosed herein. In one variation, the polymer may be crosslinked with aqueous oxidizing agents, or in an environment or condition where the pH>6.

In some embodiments, the ionic polymer glue of the present application may be used as an adhesive or a bio-glue for surgical intervention, plastic surgery, dental adhesive, bone adhesive, wet glue for tissue-tissue adhesion and bone-tissue adhesion or joints, underwater glue for bone-tissue joints, adhesive coatings for dental and medical implants, or surface primers for mineral fillers used for polymer composites including dental and bone cements, adhesives, composites or electronic devices.

General Scheme for The Preparation of Representative polymers:

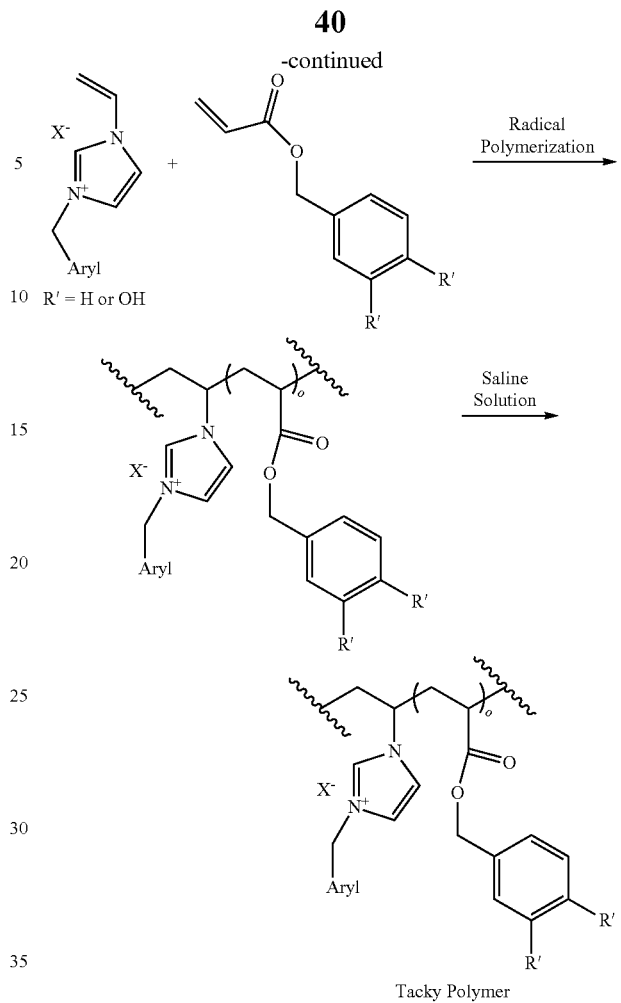

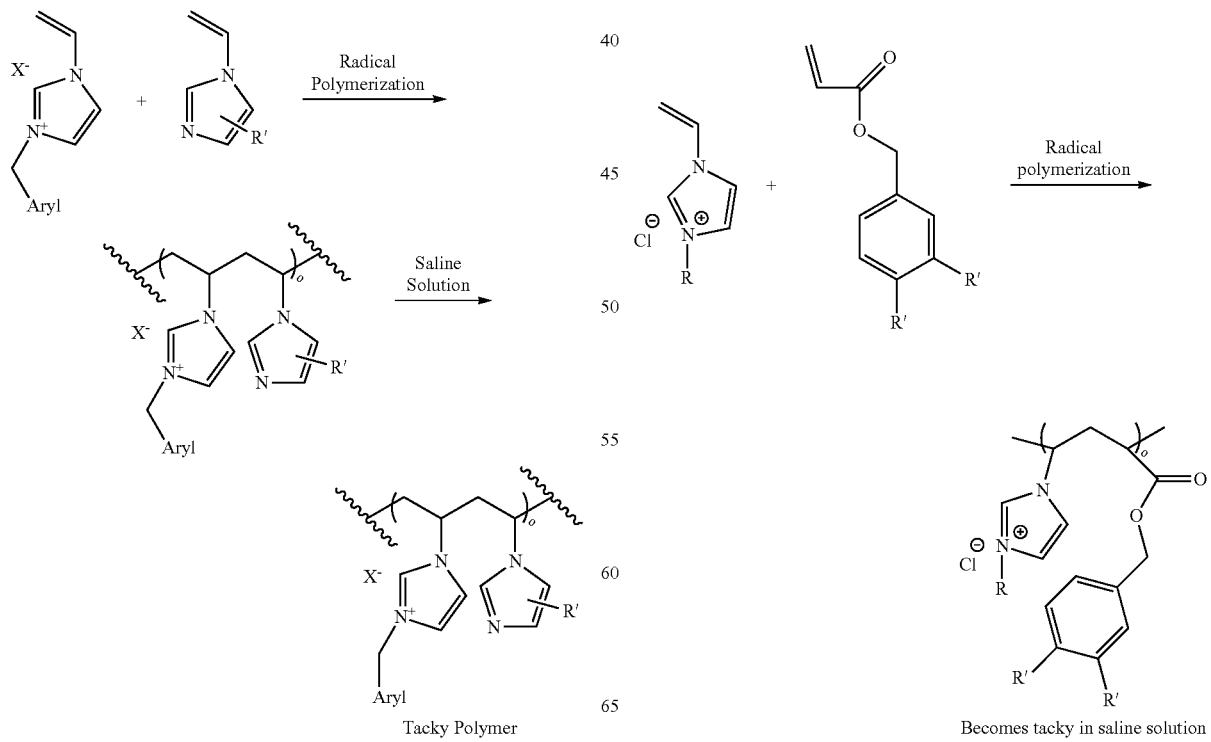

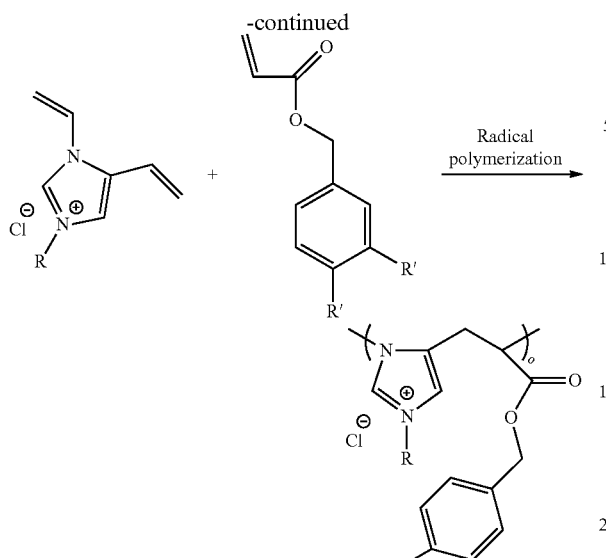

Becomes tacky in saline solution

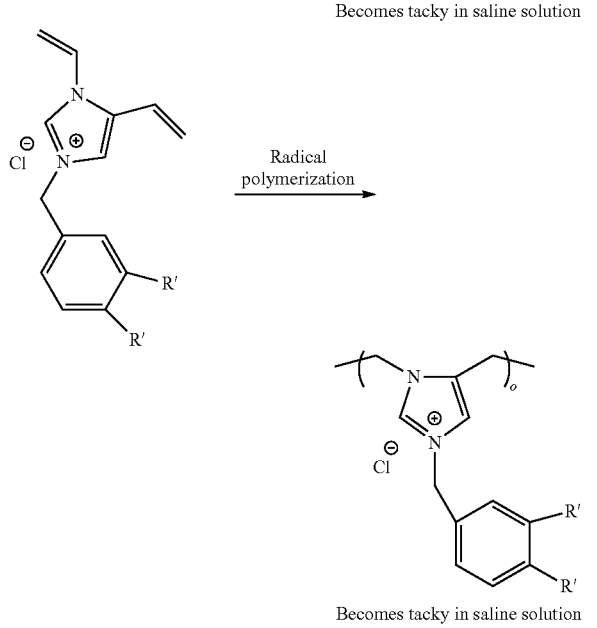

Becomes tacky in saline solution

EXPERIMENTAL

The procedures for the preparation of the homopolymers or copolymers are based on a related process for the preparation of highly conductive, mesoporous, graphitic nanostructures as described in J. Yuan et al., Chem. Mater. 2010, 22, 5003-5012.

General Procedure:

The co-monomers (for example protected catechol acrylate and 2-diethylaminoethyl acrylate) are mixed in accordance with the desired molar ratios for each application, along with a catalyst (for example, 0.01 equiv of a radical photoinitiator, e.g., acrylic acid and azobisisobutyronitrile (AIBN)) dissolved in desired solvent such as toluene/THF for non-polar co-monomers or DMF/diglyme/water for polar co-monomers.

In one particular process of using the copolymers, such as polymers comprising catechol cationic copolymers, the copolymers are prepared from a protected catechol acrylate due to the spontaneous autoxidation of the catechol functional group, or the reactions are carried in acidic conditions to generate a reducing environment (pH<5.5) for catechols. In one method, where the protecting groups are present, the silyl-protecting groups are later cleaved in an aqueous pH<3 solution at room temperature.

Visible or UV light curing system: For further crosslinking of acrylate side groups of non-acrylate copolymers (e.g., polyester with acrylate side chains) to enhance cohesion of glues, visible or UV radical polymerization are carried out.

Hand peel test: Once each adhesive film is prepared on PET backing and tested by hand. The stickiness or adhesive property of the tapes in water is stronger than stickiness of 3M Scotch packing tapes in dry ambient condition.

1-Vinyl 3-benzylimidazolium Chloride

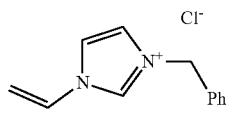

The title compound was prepared as follows: 30 ml of N-vinylimidazole (331 mmol, 1 equiv.) was added to a dry round bottom flask fitted with a rubber septa, stir bar, and argon needle. 100 ml of anhydrous MeCN was added to the flask via syringe, and stirred. Once completely dissolved, 30 ml of benzyl chloride (339 mmol, 1.02 equiv.) was added and the mixture was stirred at 65° C. for 18-24 hours under argon. The mixture was then cooled to ambient temperature, and volatiles were removed by rotary evaporation under reduced pressure to obtain a viscous oil. Traces of MeCN and excess benzyl chloride were removed by addition of diethyl ether to the flask, which was then vigorously swirled then let settle, and the ether layer was decanted off from the oil. This process of swirling with ether, settling, then decantation, was repeated several times with fresh ether until no further odor of benzyl chloride could be detected. The last traces of solvent were then removed on high vacuum to obtain the desired compound as a tan froth of bubbles in quantitative yield (73 grams, 100%).

Poly (1-vinyl 3-benzylimidazolium Chloride, HP-1)

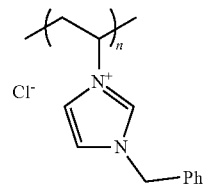

The title compound was prepared as follows: To a dry round bottom flask fitted with a stir bar, rubber septa, and argon needle was added 43.7 grams of the preceding imidazolium salt dissolved in 150 ml of anhydrous DMF. 164 mg of AIBN (azabisisobutryonitrile, 1 mmol, 0.005 equiv.) was added as a solid, and the solution was sparged with argon for 10 minutes. Once fully sparged, the flask was heated at 85° C. for 3 days, with stirring. The flask was cooled to ambient temperature, and DMF was removed by 3 rounds of coevaporation with toluene on a rotary evaporator. The polymer was purified by dissolving the crude residue in a minimum amount of methanol, and reprecipitation from THF (volume MeOH:THF=1:10), where the solid was let settle and supernatant discarded. This process of reprecipitation was repeated once more. Traces of methanol were removed by stirring the solids with THF, letting settle then decanting off the THF. This process was repeated, substituting hexanes for THF, where after decantation the solids were transferred by spatula to a round bottom flask, and traces of solvent were removed under high-vacuum to afford pure polymer.

Synthesis of Homopolymer (HP-2)

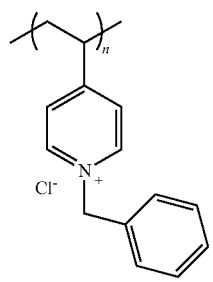

Into a 50 mL flask equipped with a magnetic stir bar under nitrogen is added the monomer 4-vinyl-1-benzylpyridinium chloride (M3, 5 g). The monomer is dissolved in 50 mL of DMF. Azobisisobutyronitrile (AIBN) initiator (100 mg) was added into the solution. The solution is then stirred at 90° C. for 20 h. The mixture is cooled to room temperature. Polymer is then precipitated and dried as described in the above procedure. About 5 g of HP-2 is obtained after the purification.

Synthesis of Copolymer, P2

Both monomers M1 and M2 are prepared according to literature methods. See for example, J. Yuan et al., Chem. Mater. 2010, 22, 5003-5012. 1-Vinyl-3-benzyl imidazolium chloride (monomer M1, 1 g) and silyl protected catechol acrylate derivative (monomer M2, 0.3 g) are added to a 250 mL 3-N RBF with a magnetic stir bar under nitrogen. The monomers are dissolved in N,N-dimethylformamide (DMF, 10 mL) and stirred at room temperature for about 15 minutes. Azobisisobutyronitrile (AIBN) initiator (13 mg) is added into the solution mixture, and the reaction mixture is stirred and heated to 80° C. for 24 h (Figure 1). After the reaction is completed, the solution is transferred to a 500 mL RBF. Diethyl ether (150 mL) is added to the stirred reaction mixture to precipitate out the crude polymer product, P1.

The resulting mixture with the solid precipitate is stirred at room temperature for 15 mins. and DMF (10 mL) is added to re-dissolve the solids. To the stirred mixture is slowly added diethyl ether (150 mL) to re-precipitate the polymer. Unreacted monomers are dissolved in the diethyl ether and are removed from the product.

The precipitated polymer is filtered with a Buchi filter funnel using Whatman paper, and the solid polymer is washed with 30 mL diethyl ether and air dried for about 1 hour. The dried polymer is transferred to a 250 mL RBF and water (10 mL) is added with stirring to dissolve the polymer. To the stirred aqueous solution of the polymer at room temperature is added 50 mL of aqueous HCl (pH=2, 0.01 M HCl prepared by dissolving 1 mL 0.5 M HCl (Sigma Aldrich) in 49 mL DI water) and stirred for 2 h, and dialyzed thoroughly as follows. The P1 polymer solution is added into dialysis tube (molecular weight cutoff: 1000), and is dialyzed against DI water (1 L) for 72 h, during which the water is exchanged with fresh DI water for 5 times. The purified polymer P1 is obtained after freeze drying as follows. P1 polymer solution is freezed at −30° C. and subsequently dried under vacuum (300 Pa pressure) for 24 h.

Synthesis of Copolymer P3 and Epoxy Curing to Form Copolymer P4 a)

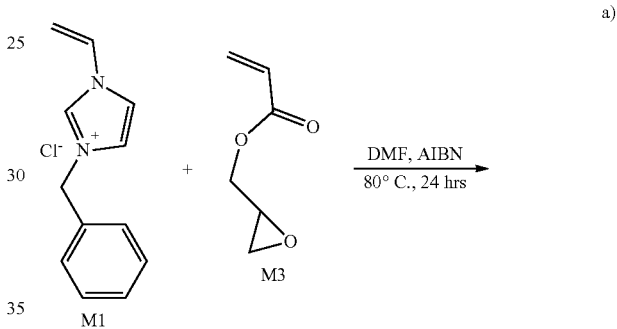

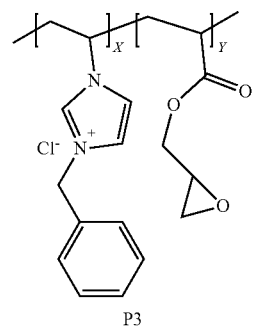

b)

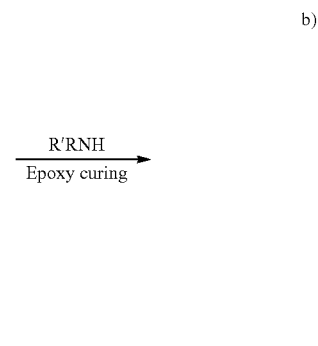

-continued

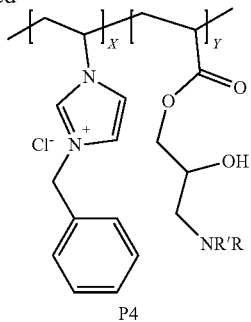

P4 wherein: x and y define the block polymer and are integer greater than 1; and R and R' are each independently H, $C_1$-$C_6$alkyl, —$CH_2C_6H_5$ wherein the alkyl and the $C_6H_5$ are optionally substituted by 1 or 2 substituents selected from the group consisting of halogen (—F, —Cl, —Br— or —I), —OH, —SH, —$SiH_2$OH, —$NH_2$, —$NO_2$, —$CH_3$, —$CF_3$, —$OCH_3$ and —$OCF_3$.

Figure 2. Synthesis of Copolymer P3 and Epoxy Curing to Form P4

Synthesis of Copolymer P3

Both monomers M1 and M3 are prepared according to literature methods. See J. Yuan et al., Chem. Mater. 2010, 22, 5003-5012. 1-Vinyl-3-benzyl imidazolium chloride (monomer M1, 1 g) and glycidyl vinyl acetate (monomer M3, 0.2 g) are added to a 250 mL 3-N RBF with a magnetic stir bar under nitrogen. The monomers are dissolved in N,N-dimethylformamide (DMF, 10 mL) and stirred at room temperature for about 15 minutes. Azobisisobutyronitrile (AIBN) initiator (13 mg) is added into the solution mixture, and the reaction mixture is stirred and heated to 80° C. for 24 h (Figure 2). After the reaction is complete, the solution is transferred to a 500 mL RBF. Diethyl ether (150 mL) is added to the stirred reaction mixture to precipitate out the crude polymer product, P3. The resulting mixture with the solid precipitate is stirred at room temperature for 15 mins and DMF (10 mL) is added to re-dissolve the solids. To the stirred mixture is slowly added diethyl ether (150 mL) to re-precipitate the polymer. Unreacted monomers are dissolved in the diethyl ether and removed from product.

The precipitated polymer is filtered with a Buchi filter funnel using Whatman paper, and the solid polymer is washed with 30 mL diethyl ether and air dried for about 1 hour. The purified polymer P3 is obtained after freeze drying as follows. P3 polymer solution is freezed at −30° C. and subsequently dried under vacuum (300 Pa pressure) for 24 h.

General Process:

A process for further crosslinking or curing process between the polymer or copolymer functional groups in the polymer chain can also effected when the polymer comprises certain crosslinkable or curable functional groups or residues. The crosslinking or curing process may provide a significantly stronger adhesive when compared to the similar polymeric adhesive composition without the additional crosslinking or curing step (e.g., P3 to P4). Such crosslinkable or curable functional group includes, for example, a vinyl group, an acrylate, an epoxide, a glycidyl, a hydroxy aryl, polyhydroxy aryl such as a catechol group.

In one embodiment, when the curable group is a hydroxy aryl group, such as a catechol group, curing of the polymer may be performed by changing the pH of the aqueous formulation comprising the polymer to a different pH, such as a more basic pH. For example, the polymer formulation may be contacted with water or an aqueous solution at a pH of about pH of 5, pH>5, pH>5.5, pH>6, pH>6.5, pH>7, pH>7.5, pH>8, pH>8.5, pH>9 or higher.

In another embodiment of the process, the materials or the surface of the materials comprising the adhesive may be first contacted or immersed in water or in an aqueous solution, and then the pH of the resulting mixture or composition may be increased to the desired pH, depending on the nature of the polymer, the functional group and the nature of the materials being glued together. Without being bound by the proposed mechanism of action disclosed herein, it is believed that the polymer or the functional groups, such as a hydroxy aryl group, undergo a curing or crosslinking process by way of an auto-oxidative crosslinking process or may be initiated by a metal ion(s) via coordination chemistry; to form a significantly stronger adhesive when compared to the use of the adhesive without a curing step. In another embodiment where the polymer comprises a functional group or residue such as an acrylate, a methacrylate or a substituted acrylate, the polymer may be crosslinked via visible light or UV light via photoinitiated polymerization.

In another embodiment, when the polymer comprises an epoxy group, such as an epoxide or a glycidyl group, the curing step may be performed using an a reagent, such as an amine. Such an amine may be a di- or tri-amine based epoxy curing agent. Amines that may be used for amine-based epoxy curing includes aliphatic amines such as diethylamine (DEA), methylamine (MA), dimethylamine (DMA), cycloaliphatic amines such as cyclohexylamine (CHA) and cyclohexylmethylamine (CHMA), and aromatic amines such as aniline (AA) and methylaniline (MAA). Such a curing process is similar to that of the method for curing epoxy resin, where the adhesive maybe prepared or mixed and cured immediately before applying the adhesive to attach two surfaces. In one method, the dried polymer is transferred to a 250 mL RBF and water (10 mL) is added with stirring to dissolve the polymer. To the stirred aqueous solution of the polymer at room temperature is added diethylamine (DEA) and allowed to cure.

Performance of Adhesive Compositions with Different Materials:

Preparation of the Adhesive Composition:

1 g of the homopolymer or the copolymer was added into a 50 mL RBF with a magnetic stirrer. 10 mL of water was added to the homopolymer or copolymer and the resulting mixture was stirred for 15 minutes to form a milky white, relatively viscous adhesive composition. The adhesion experiments described below may employ the polymer adhesive composition.

For the copolymers that are functionalized with extra crosslinkable residues, optionally, there is a second step of curing of the adhesive composition that may be performed to increase or enhance the bonding performance. For example, in the case of the preparation of copolymers with catechol functional groups (i.e., 3,4-dihydroxyphenyl-), a catechol-mediated auto-oxidation process may be performed.

Accordingly, in addition to joining two test strips of the same or different material composition, the strips (or materials) may be immersed in water, at a pH of about 5, pH>5, pH>5.5, pH>6, pH>7, pH>8, pH>9, or pH range of 8-9, the polymer undergoes further curing or crosslinking to form a stronger adhesive. Under certain conditions, the catechol or other hydroxy benzyl or hydroxy aryl groups may undergo auto-oxidative crosslinking above neutral pH, such as pH>7.

Depending on the type or the nature of the functional groups of the polymers as described herein, the curing step may also be performed by crosslinking mechanism or chemistry. For example, where the polymer comprises a hydroxyphenyl group or dihydroxyphenyl group such as a catechol group, the crosslinking process may be initiated by a metal ion(s) by way of coordination chemistry. The pH of the solution may be lower than pH 5.5, the concentration should be considered with respect to solubility, stoichiometry, and the nature of the metal ion may affect the crosslinking process.

The adhesive may also be soluble in pure water or in the presence of saline or a saline solution. For example, the salt solution may comprise of a single salt or a mixture of salts, including NaBr, NaCl, NaI, LiBr, LiCl and LiI. In one particular aspect, the higher salt concentration (body fluid or sea water) in the applied media will cause a drying effect of the polymer when polymer solution in pure water or aqueous salt solution at low concentration is applied to surfaces in aqueous salt solution at higher concentration such as body fluid, salt water or sea water.

Two strips of pork tissues of about 1 inch long, half inch wide and about ⅛ inch thick are immersed in a saline solution for about 10 seconds. While leaving the dermises immersed in the saline solution, approximately 1 mL of the adhesive composition is drawn up into a pipette and injected or delivered onto one surface of the first of the two tissues to form a milky white layer of adhesive of about 2-3 square centimeters on the surface. While still immersed in the saline solution, one surface of the second tissue surface is brought into contact with the first tissue surface with the layer of adhesive and the two tissues are lightly pressed together for about 2 seconds, and then released. The resulting tissues are then glued together in the saline solution.

Two strips of plastics (made of PVC, polyethylene or polyurethane) of about 1 inch long, half inch wide and about ¼ inch thick are immersed in a saline solution for about 10 seconds. While leaving the plastic strips immersed in the saline solution, approximately 1 mL of the adhesive composition is drawn up into a pipette and injected or delivered onto one surface of the first of the two plastic strips to form a milky white layer of adhesive of about 2-3 square centimeters on the surface. While still immersed in the saline solution, one surface of the second plastic strip is brought into contact with the first plastic strip with the layer of adhesive and the two plastic strips are pressed together with a thumb and index finger for about 2 seconds, and then released. The resulting two plastic strips are then sealed or glued together.

The glues adhere all the different type of materials and surfaces including tissue to tissue, tissue to metal, tissue to plastic, tissue to mineral, mineral to metal, mineral to plastic, metal to metal, metal to plastic, plastic to plastic, mineral to mineral, and among other materials in wet conditions including under water. Such materials include tissues, such as human tissues, animal tissues, skin, tooth enamel, dentine, metals such as aluminum, stainless steel, copper, brass, glass, plastic, and combinations of these materials.

This solution can also be used as a low tack reusable adhesive (such as Post-It® notes). Such low tack or pressure sensitive adhesives may exhibit a low level of adhesion when first applied and may remove cleanly from a surface. In one aspect, the solution comprise of water, ethanol, NaCl, and the adhesive compound. As an example for preparing the reusable and sprayable low-tack pressure-sensitive adhesive solution, the adhesive compound is dissolved in water at 1-30 w/v % concentration, then the solution is diluted with ethanol to 10% to 90%. Saturated NaCl aqueous solution (1-30%) is then added. This solution can be sprayed on or applied to any surfaces that need to be low tack or anti-slippery under moist or wet conditions.

As another example, M2 can be replaced with vinyl alcohol. After copolymerization, the alcohol side group may be modified to acrylate or methacrylate by reaction with acryloyl chloride or methacryloyl chloride via acryl chloride esterification by nucleophilic addition-elimination with alcohol. The substituted acrylate or methacrylate residues can be crosslinked via radical polymerizations.

While the foregoing description describes specific embodiments, those with ordinary skill in the art will appreciate that various modifications and alternatives can be developed. Accordingly, the particular embodiments described above are meant to be illustrative only, and not to limit the scope of the invention, which is to be given the full breadth of the appended claims, and any and all equivalents thereof.

What is claimed:

1. A method for sealing a first object having a surface to a second object having surface, the method comprising:
   1) applying an adhesive to the surface of the first object;
   2) contacting the surface of the first object comprising the adhesive with the surface of the second object for a sufficient period of time until the first and second object forms a seal;
   wherein the adhesive is an adhesive composition comprising a polymer of the formula A or B:

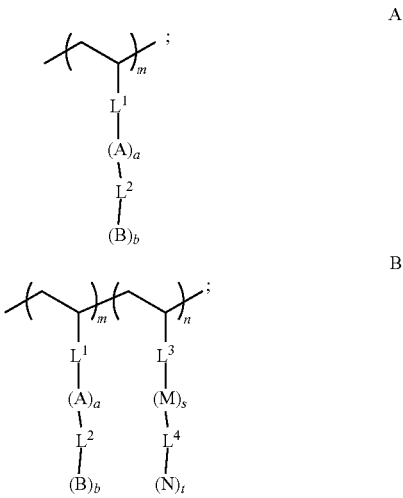

wherein:
each m and n is independently 100 to 1,000,000;
each a, b, s and t is independently 0, 1 or 2;
each $L^1$, $L^2$, $L^3$ and $L^4$ is independently absent or is independently selected from —$CH_2$—, —O—, —S—, —$(CH_2)_{1-2}$—, —$CH(CH_2\text{-})_2$, —C(O)O—, —C(O)OCH$_2$—, —$CH_2C(O)O$—, —$CH_2C(O)NH$—, —C(O)NHCH$_2$—, —C(O)NH— and —NR'— where R' is selected from H, —$CH_3$, —$CH_2CH_3$ and —$CH_2C_6H_5$ or substituted benzyl, or a bond;

each A, B, M and N is independently absent or is independently selected from the group consisting of an aryl, substituted aryl, heteroaryl, substituted heteroaryl, heteroarylammonium $X^-$ and substituted heteroarylammonium $X^-$, wherein each $X^-$ is independently a counter anion selected from the group consisting of $Cl^-$, $Br^-$, $I^-$, $-SO_4^{-2}$ and $-PO_4^{-3}$; provided that not all of $L^1$, $L^2$, $L^3$ and $L^4$ and A, B, M and N are absent;

wherein the first object is dermis and the second object is selected from the group consisting of a metal, a metal oxide, a mineral, mica, silicon, glass, calcium, enamel, bone, steel, tooth enamel, tooth dentin, hydroxylapatite, kaolin and zirconia.

2. The method of claim 1, wherein the method further comprises the addition of saline, salt or a mixture of salt to increase the salinity.

3. The method of claim 2, wherein the salt is selected from the group consisting of NaBr, NaCl, NaI, LiBr, LiCl and LiI.

* * * * *